United States Patent [19]
Bornzin et al.

[11] Patent Number: 5,540,725
[45] Date of Patent: Jul. 30, 1996

[54] UPPER RATE RESPONSE FOR IMPLANTABLE PACEMAKER BASED ON ATRIAL LOCK INTERVAL PACING

[75] Inventors: Gene A. Bornzin, Camarillo; Brian M. Mann, Beverly Hills, both of Calif.

[73] Assignee: Pacesetter, Inc., Sylmar, Calif.

[21] Appl. No.: 500,731

[22] Filed: Jul. 11, 1995

[51] Int. Cl.⁶ ............................................. A61N 1/368
[52] U.S. Cl. ........................................................ 607/009
[58] Field of Search .................................... 607/9, 14, 24

[56] References Cited

U.S. PATENT DOCUMENTS

| | | |
|---|---|---|
| 4,712,555 | 12/1987 | Thornander et al. . |
| 4,788,980 | 12/1988 | Mann et al. . |
| 4,809,697 | 3/1989 | Causey, III et al. . |
| 4,815,469 | 3/1989 | Cohen et al. . |
| 4,847,617 | 7/1989 | Silvian ............................ 340/870.160 |
| 4,940,527 | 7/1990 | Mann et al. . |
| 4,944,297 | 7/1990 | Sholder . |
| 5,097,832 | 3/1992 | Buchanan . |
| 5,156,147 | 10/1992 | Warren et al. . |
| 5,178,151 | 1/1993 | Sackner . |
| 5,269,299 | 12/1993 | Duncan . |

OTHER PUBLICATIONS

Haskell, Richard J., et al. "Optimum AV Interval in Dual Chamber Pacemakers", PACE, vol. 9, pp. 670–675. (Sep.–Oct. 1986).

Primary Examiner—William E. Kamm
Assistant Examiner—Scott M. Getzow
Attorney, Agent, or Firm—Lisa P. Weinberg

[57] ABSTRACT

Atrial lock interval pacing increases stroke volume and optimizes cardiac output by providing a modified P-wave tracking mode that tracks P-waves up to a maximum instantaneous tracking rate only for short periods of time, to provide a maximum instantaneous ventricular heart rate, yet limits the maximal mean (or average) ventricular rate over a longer period of time, to provide a safe target maximal average rate. Two main types or embodiments of modified P-wave tracking modes may be used. A first provides a sequence of timed intervals that begins upon sensing each P-wave. Such sequence may include, e.g.: (1) a PV interval; (2) a PVARP; (3) a Wenkebach interval; (4) an atrial lock interval; and (4) a P-track interval. P-waves are not tracked during the PV interval or PVARP. P-waves that occur during the Wenkebach or Atrial lock interval are tracked, but not in a conventional manner. P-waves that occur during the P-track interval are tracked in a conventional manner. A second modified P-wave tracking mode defines a maximum mean rate (MMR) interval. The MMR interval (MMRI) is an asynchronous free-running signal that is not synchronized to any cardiac cycle events. During each MMRI, the number of atrial or ventricular events that occur are noted. Ventricular stimulation pulses (V-pulses) are not generated if the resulting ventricular depolarization would represent the second ventricular depolarization of the current MMRI.

45 Claims, 20 Drawing Sheets

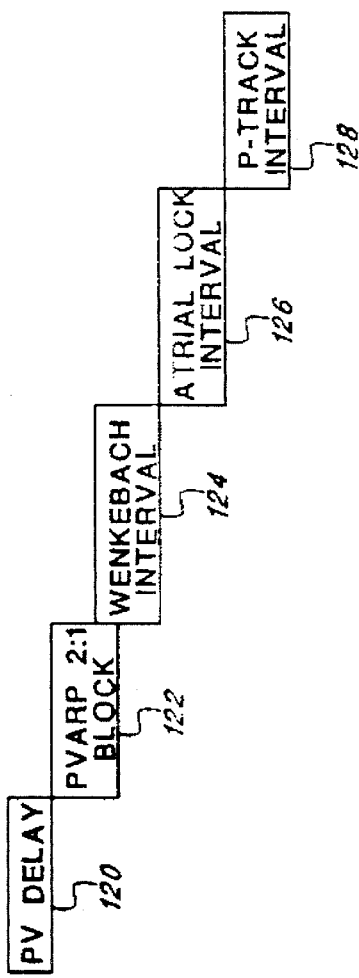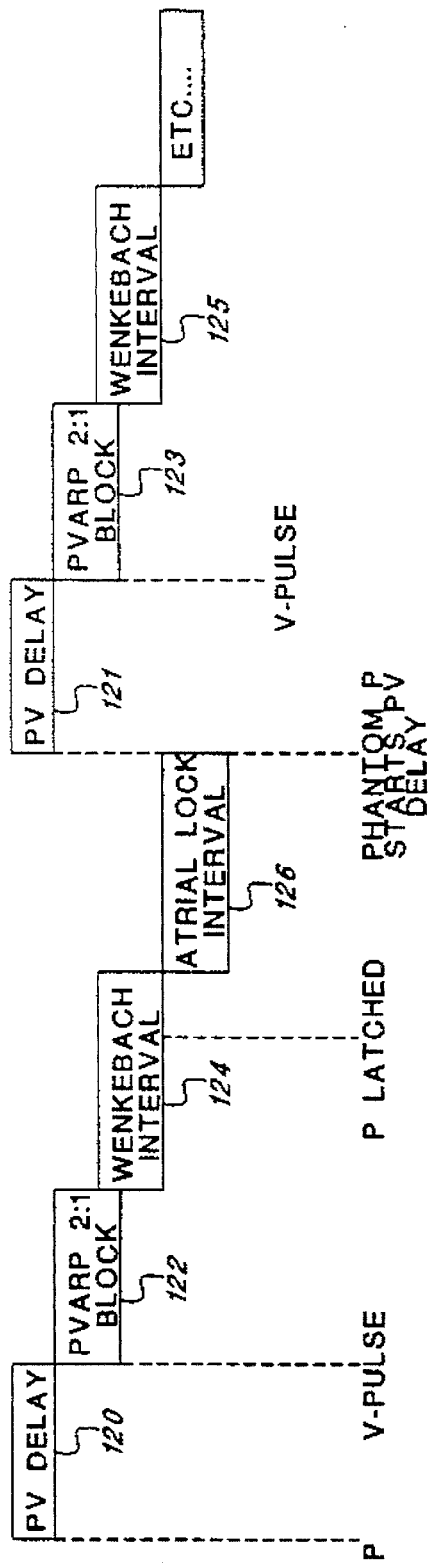

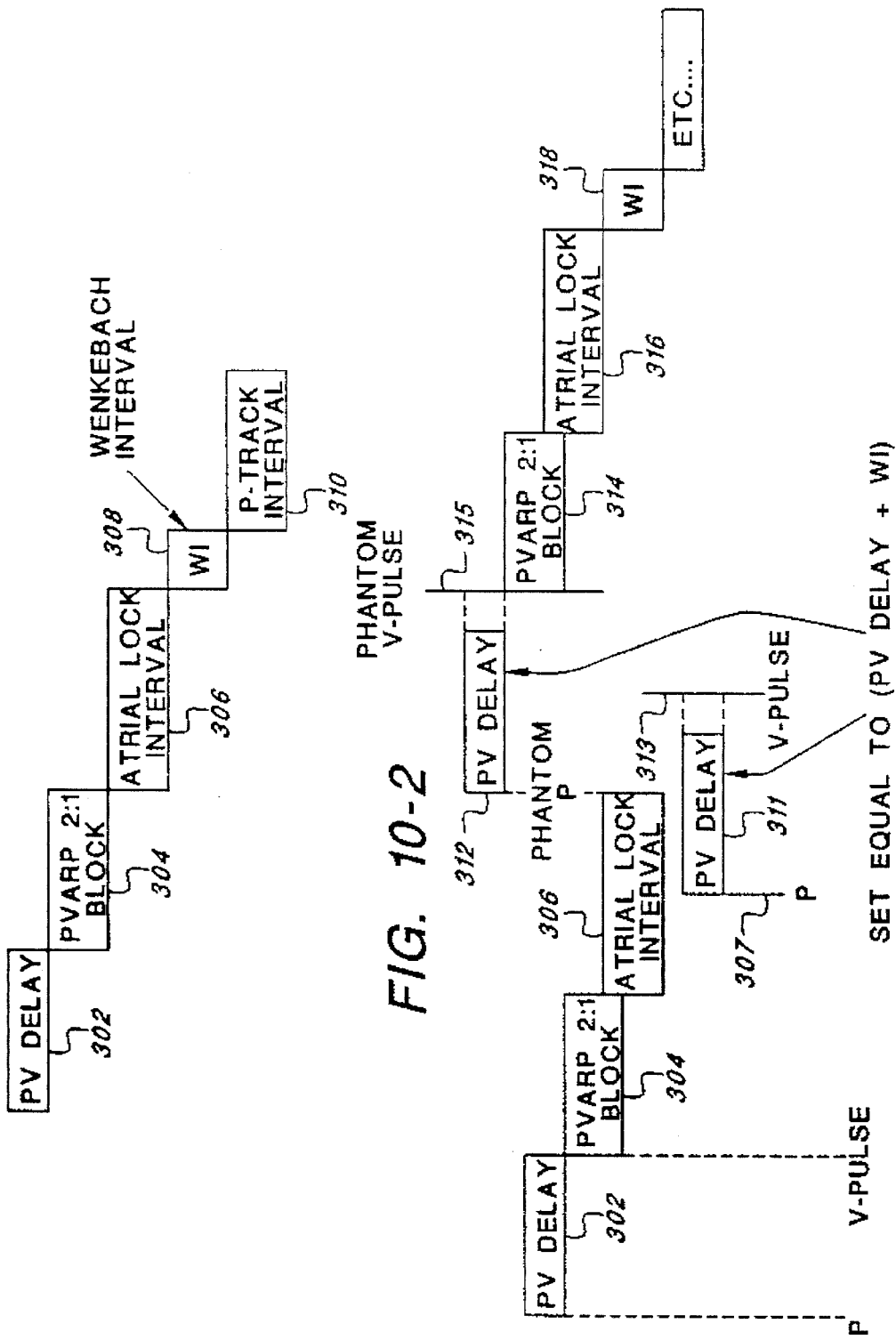

UPPER RATE RESPONSE FOR IMPLANTABLE PACEMAKER BASED ON ATRIAL LOCK INTERVAL PACING

BACKGROUND OF THE INVENTION

FIELD OF THE INVENTION

The present invention relates to implantable medical devices and methods, and more particularly to a dual-chamber implantable pacemaker or pacemaker system having an improved upper rate response adapted to synchronize the atrium of a patient's heart with the ventricle for a higher percentage of the time, thereby enhancing the upper rate cardiac output.

The basic function of the heart is to pump (circulate) blood throughout the body. The blood serves as a medium for delivering oxygen and nutrients to the various tissues while removing waste products and carbon dioxide. The heart is divided into four chambers comprised of two atria and two ventricles. The atria are the collecting chambers holding the blood which returns to the heart until the ventricles are ready to receive this blood. The ventricles are the primary pumping chambers. The pumping function of the heart is achieved by a coordinated contraction of the muscular walls of the atria and the ventricles.

The atria are more than simple collecting chambers. The atria contain the heart's own (natural, native or intrinsic) pacemaker that controls the rate at which the heartbeats or contracts. In addition, the atrial contraction helps to fill the ventricle, further contributing to optimal filling and thus maximizing the amount of blood which the heart is able to pump with each contraction. Thus, atrial contraction is followed after a short period of time (normally 120 to 200 ms) by ventricular contraction.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This is termed AV synchrony.

A cardiac cycle comprises one sequence of systole and diastole. It can be detected by counting the patient's pulse rate. It is also reflected by the cardiac rhythm as recorded by an electrocardiogram (ECG) or electrogram (EGM). The ECG is a recording of the electrical activity of the heart as seen using surface electrodes placed on the surface of the body. The EGM is a recording of the electrical activity of the heart as seen using electrodes placed within the heart. The electrical activity refers to the cardiac depolarization in either the atrium and/or ventricle. In general, on the ECG or EGM, the atrial depolarization is represented by a P-wave, while the ventricular depolarization is represented by a QRS complex, usually abbreviated as an "R-wave". The electrical depolarization triggers or initiates the active muscular contraction. Once the cardiac cells are depolarized, they must repolarize in order for the next depolarization and contraction to occur. Ventricular repolarization is represented by the T-wave. Atrial repolarization is rarely seen on an ECG or EGM as it occurs at virtually the same time as the R-wave, and is thus hidden by this large electrical signal.

A normal heart rate varies between 60 to 100 beats per minute (bpm) with an average of 72 bpm resulting in approximately 100,000 heartbeats per day.

The amount of blood that the heart pumps in one minute is called the cardiac output. It is calculated by the amount of blood ejected with each heartbeat (stroke volume) multiplied by the number of heartbeats in a minute. If the heart rate is too slow to meet the physiologic requirements of the body, the cardiac output will not be sufficient to meet the metabolic demands of the body. Too slow of a heart rate, termed a bradycardia, may thus result in one of two major symptoms: (1) if the heart effectively stops with no heartbeat, there will be no blood flow and if this is sustained for a critical period of time (10 to 30 seconds), the individual will faint; or (2) if there is a heartbeat but it is too slow, the patient will be tired and weak (termed low cardiac output).

A pacemaker is a medical device that is used to selectively stimulate the heart with electrical stimulation pulses aimed at assisting it to perform its function as a pump. Normally, the stimulation pulses are timed to keep the heart rate above a prescribed limit, i.e., to treat a bradycardia. A pacemaker may thus be considered as a pacing system. The pacing system is comprised of two major components. One component is a pulse generator which generates the stimulation pulse and includes the electronic circuitry and the power cell or battery. The other is the lead or leads which electrically couple the pacemaker to the heart.

The pacemaker delivers an electrical stimulus to the heart to cause the heart to contract when the patient's own intrinsic rhythm fails. To this end, pacemakers include sensing circuits that sense the EGM, and in particular that sense the P-waves and/or R-waves in the EGM. By monitoring such P-waves and/or R-waves, the pacemaker circuits are able to determine the intrinsic rhythm of the heart, and provide stimulation pulses that force atrial and/or ventricular depolarization at appropriate times in the cardiac cycle so as to help stabilize the electrical rhythm of the heart.

Pacemakers are described as either single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

A three letter code (sometimes expanded to a four or five letter code) is used to describe the basic mode in which the pacemaker is operating. The first three letters refer specifically to electrical stimulation for the treatment of bradycardia, with the first letter indicating the chamber(s) of the heart where the electrical stimulus is delivered (A=atrium; V=ventricle; D=dual or both), the second letter identifying the chamber(s) in which sensing occurs, and the third letter identifying the way a pacemaker responds to a sensed signal (I=inhibited; T=trigger; D=dual or both sensing responses). A fourth position (when used) identifies the degree of programmability and rate modulation, and a fifth position (when used) refers to electrical stimulation therapy for the primary treatment of fast heart rhythms or tachyarrhythmias or tachycardias.

A popular mode of operation for dual-chamber pacemakers is the DDD mode. Specifically, DDD systems provide atrial pacing during atrial bradycardia, ventricular pacing during ventricular bradycardia, and atrial and ventricular pacing during combined atrial and ventricular bradycardia. In addition, DDD systems provide an atrial synchronous mode. Such features more closely approximate the normal response to exercise, or other physiological activity demanding a faster heart rate, by permitting a rate increase to occur commensurate with the rate of the sensed P-wave. This advantageously increases cardiac output and facilitates maintenance of AV synchrony.

Most implantable pacemakers also include some type of upper rate limiting feature to prevent the pacemaker from providing stimulation pulses at a rate that exceeds a prescribed upper rate limit. Such upper rate limit is usually referred to as a "Maximum Tracking Rate", or MTR. The response to upper rate limiting is commonly referred to as Pacemaker Mediated "Wenkebach" Phenomenon.

When Pacemaker Mediated "Wenkebach" Phenomenon occurs, two major consequences usually result. First, when the atrial rate exceeds the MTR, then the PV interval may be prolonged to prevent stimulation at rates exceeding the MTR. The effect is a prolonging of the A-V interval, or the interval between atrial activity and ventricular activity. Second, a P-wave may occasionally occur during the post ventricular atrial refractory period (PVARP), which period immediately follows a V-pulse. P-waves that occur during PVARP are ignored. Hence, it is necessary to wait for the next P-wave to occur before a V-pulse is triggered after a PV interval. The effect is a prolongation of the V-to-V interval to an interval that is longer than the MTR interval (MTRI), where the MTRI=1/MTR when the MTR is expressed in cardiac cycles per second. Either effect above is hemodynamically deleterious. That is, the consequence of a prolonged A-V interval is that the cardiac output decreases because of loss of proper timing of the "atrial kick". Moreover, the occasional prolonging of the V-to-V interval results in the average heart rate being less than the rate available at the MTR. Further, at very high atrial rates or when PVARP is relatively long, the upper rate behavior appears as a 2:1 or higher block (i.e., every other, or every nth, P-wave is blocked by PVARP and is thus not recognized). The consequence is a ventricular rate that is usually ½ of the atrial rate. Such a low ventricular rate, even though the "atrial kick" remains intact (at least one-half of the time), can also be very deleterious hemodynamically. In addition, if the unsensed P-wave occurs during systole, then mitral or tricuspid regurgitation may occur. Such regurgitation further degrades hemodynamic performance.

In addition to the above-described degradation of hemodynamic performance caused by prolongation of the PV interval, a prolongation of the PV interval also problematically affects the electrophysiologic performance of the pacemaker/cardiac system. That is, a prolongation of the PV interval enhances the probability of retrograde conduction, as does the upper rate limiting provided by Wenkebach performance. Retrograde conduction, in turn, leads to a much greater susceptibility to a pacemaker mediated tachycardia (PMT). What is needed, therefore, is an improved upper rate performance that does not require the PV interval to be lengthened, but rather preserves the PV interval at a fixed value, thereby reducing the likelihood of retrograde conduction, and minimizing the susceptibility of the pacemaker/cardiac system to a PMT.

The present invention advantageously addresses the above and other needs.

SUMMARY OF THE INVENTION

The present invention provides a dual-chamber implantable pacemaker that achieves improved upper rate performance by synchronizing the atrium with the ventricle for a higher percentage of the time, thereby increasing stroke volume and optimizing cardiac output. Such synchronization is achieved by operating the pacemaker in a modified P-tracking mode that tracks P-waves up to a maximum instantaneous tracking rate only for short periods of time, thereby providing maximum instantaneous ventricular heart rate, yet limits the maximal mean (or average) ventricular rate over a longer period of time (e.g., one minute) to a value that is less than or equal to a maximum mean rate (MMR).

The improved upper rate performance of a pacemaker operating in accordance with the present invention is referred to as "atrial locked interval" pacing. Atrial locked interval pacing is achieved by operating the pacemaker in a modified P-tracking mode. A P-tracking mode is simply a mode during which sensed P-waves are "tracked" by having a ventricular stimulus follow each sensed P-wave after a PV delay or PV interval, unless an R-wave is sensed prior to the termination of the PV delay. (Note: as used herein, the term "PV delay" is synonymous with "PV interval".)

In accordance with the present invention, at least two embodiments of modified P-tracking modes are contemplated, each of which may be implemented in more than one way (i.e., there are variations of each embodiment). Each embodiment may be implemented in the pacemaker as a programmable option or as a factory setting.

In a first modified P-wave tracking mode embodiment, a sequence of timed intervals begin at the sensing of each P-wave, and define the pacing cycle. Such sequence of timed intervals may include, e.g.: (1) a PV interval, following which a V-pulse is generated; (2) a post ventricular atrial refractory period (PVARP); (3) a Wenkebach interval; (4) an atrial lock interval; and (4) a P-track interval. P-waves are not sensed, i.e., not tracked, should they occur during the PV interval or PVARP. P-waves that occur during the Wenkebach interval or Atrial lock interval are tracked, as explained below, but not in a conventional manner. P-waves that occur during the P-track interval are tracked in a conventional manner.

If a P-wave is sensed during the Wenkebach interval, then a P-wave signal is latched and a phantom P-wave is assumed to occur at the conclusion of the Atrial lock interval. This phantom P-wave triggers the beginning of a new cardiac cycle, i.e., a new PV delay, following which a V-pulse is generated, following which PVARP is initiated, and so on. In this way, the P-wave-during-the-Wenkebach interval is tracked, but not at a rate that exceeds 1/(PVI+PVARP+WI+ALI) where PVI is the PV interval or delay, WI is the Wenkebach interval, and ALI is the atrial lock interval.

If a P-wave occurs during the atrial lock interval, then such P-wave is tracked, i.e., a new PV delay is immediately started, following which a V-pulse is generated. However, in order to limit the maximum mean ventricular rate, the next PVARP is not started until after a phantom PV delay has elapsed which begins at the conclusion of the atrial lock interval during which the P-wave is tracked. In this way, the mean Ventricular rate for P-waves tracked during the ALI approaches or remains below the rate described by 1/(PV+PVARP+WI+ALI).

P-waves that occur during the P-track interval are tracked in conventional manner. That is, a sensed P-wave during the P-track interval triggers the beginning of a new cycle comprising: a PV delay, after which a V-pulse is generated, followed by PVARP, followed by the Wenkebach interval, followed by the atrial lock interval, and followed by another P-track interval.

Variations of the first modified P-wave tracking mode embodiment include: (1) reversing the WI and ALI in the sequence of timed intervals that define the pacing cycle, so that the sequence comprises the PVI, followed by the PVARP, followed by the ALI, followed by the WI, followed by the P-track interval; or (2) starting the PVI, in response to a sensed P-wave, at the conclusion of the WI, rather than at the end of the ALI, as in the first embodiment described above.

In a second modified P-wave tracking mode embodiment, a maximum mean rate interval (MMRI) is defined to be equal to 1/MMR and is allowed to free run without being synchronized to the cardiac cycle of any sensed events. That is, the MMRI is an asynchronous signal that is simply defined by one MMRI followed by another. During each pacing cycle, the number of atrial or ventricular events that happen to occur during the current MMRI are noted. In a first variation of this free-running embodiment, ventricular stimulation pulses (V-pulses) are not generated if the resulting ventricular depolarization would represent the second ventricular depolarization of the current MMRI. In a second variation of the free-running embodiment, only the first P-wave within the current MMRI is tracked. In either variation, the result is the same: the ventricular stimulation rate is limited to a rate that, on average, is the same as the rate of the MMRI signal.

Advantageously, in either the first or second embodiments of the modified P-wave tracking modes described above, or their variations, the maximum instantaneous tracked heart rate is 1/(PVI+PVARP+WI). Thus, P-wave tracking may occur for short periods of time up to this maximum instantaneous rate. However, over the long term (e.g., for time periods longer than about one minute), the maximal mean heart rate (MMR) will be something less than the instantaneous rate. For the first embodiment of the modified P-wave tracking mode, for example, the maximal mean heart rate approaches 1/(PVI+PVARP+WI+ALI). For the second embodiment (free-running MMRI) of the modified P-wave tracking mode, the maximal mean heart rate matches 1/MMRI. Hence, while the ventricular heart rate is limited to an appropriate mean or average upper rate, the present invention allows it to exceed the maximum mean rate for short periods of time while still tracking sensed P-waves. The result is that P-waves and V-pulses remain synchronized more often at the upper rate limits of the pacemaker, thereby increasing stroke volume and improving cardiac output. Such synchronizing also minimizes the likelihood of retrograde conduction.

It is a feature of the present invention to provide a pacemaker that offers improved upper rate performance, i.e., that synchronizes the atrium with ventricle for a higher percent of the time (higher than "Pacemaker Mediated Wenkebach"), thereby increasing stroke volume and minimizing retrograde conduction.

It is another feature of the invention to provide upper rate limiting in a P-wave tracking mode that limits the average ventricular rate to a maximum mean rate, yet allows short term P-wave tracking (and hence an instantaneous ventricular rate) that exceeds the maximum mean rate.

It is a further feature of the invention, in accordance with one embodiment thereof, to provide upper rate limiting that is achieved with a "floating" or "free running" MMRI interval signal, i.e., an asynchronous MMRI signal, that is not triggered or controlled by cardiac events.

It is an additional feature of the invention to provide reliable upper rate limiting in an implantable dual-chamber pacemaker that is easy and inexpensive to implement, requiring a minimum amount of hardware and/or software components.

BRIEF DESCRIPTION OF THE DRAWINGS

The above and other aspects, features and advantages of the present invention will be more apparent from the following more particular description thereof, presented in conjunction with the following drawings wherein:

FIG. 9-1 is a timing diagram that illustrates the various timing intervals, including an atrial lock interval (ALI), that are used to define a pacing interval in accordance with a first variation of the first modified P-wave tracking mode of the present invention;

FIG. 9-2 is a timing diagram that illustrates the response of a pacemaker in accordance with the first variation of the modified P-wave tracking mode of FIG. 9-1 when a P-wave occurs during the Wenkebach interval;

FIG. 9-3 is a timing diagram that depicts the response of a pacemaker in accordance with the first variation of the modified P-wave tracking mode of FIG. 9-1 when a P-wave is sensed-during the atrial lock interval;

FIG. 10-1 is a timing diagram that illustrates the various timing intervals, including an atrial lock interval (ALI), that are used to define a pacing interval in accordance with a second variation of the first modified P-wave tracking mode of the present invention;

FIG. 10-2 is a timing diagram that illustrates the response of a pacemaker in accordance with the second variation of the modified P-wave tracking mode of FIG. 10-1 when a P-wave occurs during the atrial lock interval;

FIG. 10-3 is a timing diagram that depicts the response of a pacemaker in accordance with the second variation of the modified P-wave tracking mode of FIG. 10-1 when a P-wave is sensed during the Wenkebach interval;

FIGS. 13-1 and 13-2 depict a flowchart that illustrates the manner in which a pacemaker carries out atrial lock interval pacing as shown in FIGS. 8–10;

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker that provides atrial lock interval (ALI) pacing in an attempt to improve stroke volume when the pacemaker is operating at or near its upper rate limits. In describing the present invention, reference will first be made to FIG. 1, where a functional block diagram of a dual-chamber pacemaker 10 is illustrated. Such functional diagram is used to initially teach the primary functions carried out by a dual-chamber pacemaker. Various embodiments of the actual components used within the pacemaker 10 to carry out the pacemaker functions will then be described in conjunction with FIGS. 2–5. The basic pacing cycle and prior techniques used to limit the upper rate performance of a pacemaker will then be briefly described in connection with FIGS. 6 and 7. Next, techniques or methods used by the pacemaker 10 to implement the present invention will be described in conjunction with FIGS. 8–15. Finally, the results achieved using the present invention will be presented in conjunction with the graphs of FIGS. 16–19.

Advantageously, a wide variety of dual-chamber pacemaker configurations and pacemaker components and/or hardware may be used to implement the invention. The descriptions that follow are only exemplary of a few such configurations.

Figure 1:
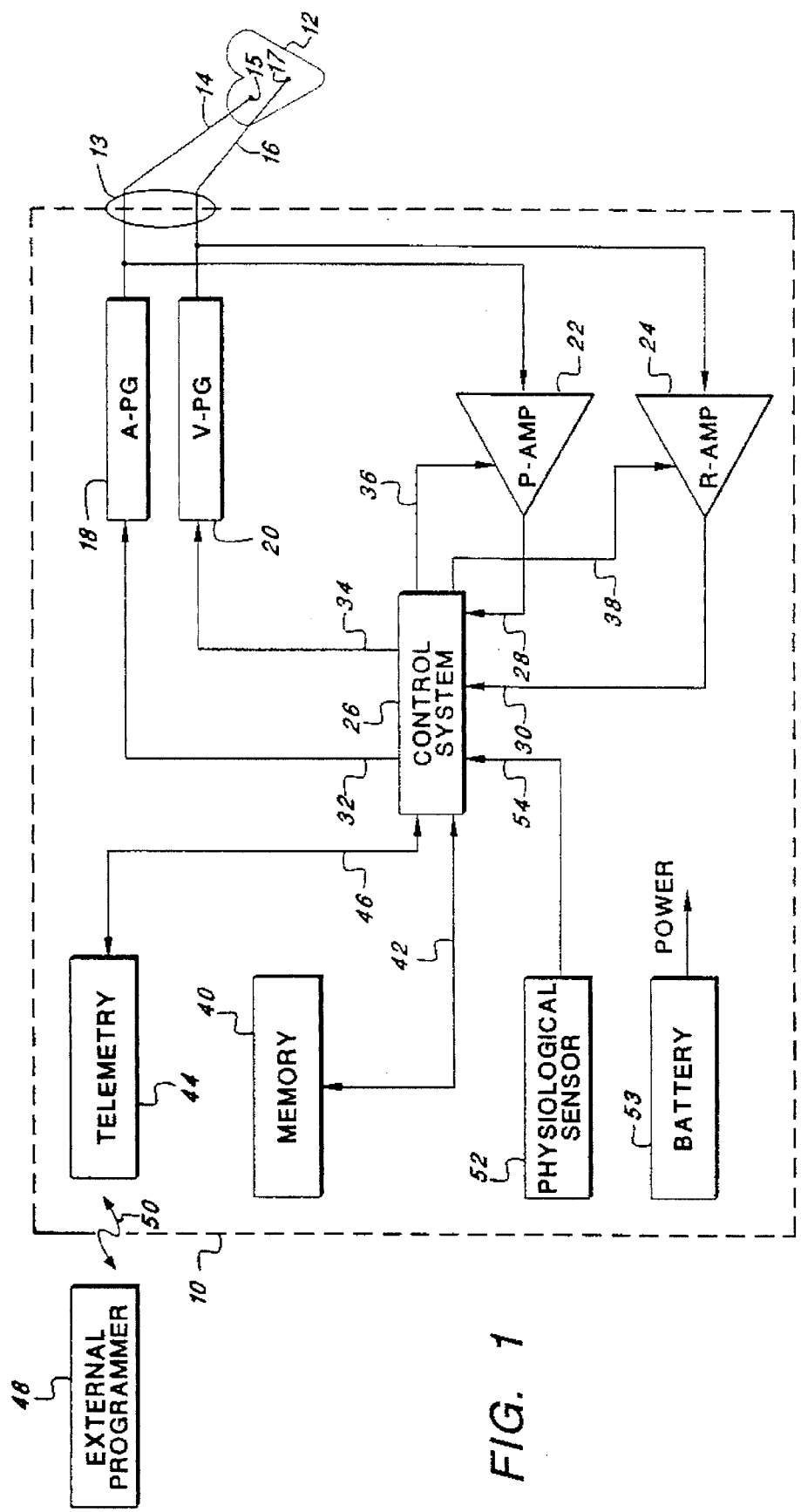
FIG. 1 is a functional block diagram of an implantable dual-chamber pacemaker.

Referring first to FIG. 1, a pacemaker 10 is coupled to a heart 12 by way of leads 14 and 16. (Note, in subsequent figures, e.g., FIG. 2, the leads 14 and 16 are referred to as the lead system 19.) The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a control circuit or control system 26. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also helps prevent residual electrical signals present in the muscle tissue as a result of the pacer stimulation from being interpreted as P-waves or R-waves.

Still referring to. FIG. 1, the pacemaker 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI) and the maximum mean rate interval (MMRI). Further, data sensed during the operation of the pacer may be stored in the memory 40 for later retrieval and analysis.

A telemetry circuit 44 is further included in the pacemaker 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50. The communication link 50 may be any suitable electromagnetic link, such as an RF (radio frequency) channel, inductive coupling, or the like. Advantageously, through the external programmer 48 and the communication link 50, desired commands may be sent to the control system 26. Similarly, through this communication link 50 and the programmer 48, data (either held within the-control system 26, as in a data latch, or stored within the memory 40), may be remotely received from the pacer 10. In this manner, noninvasive communications can be established from time to time with the implanted pacer 10 from a remote, non-implanted location. Many suitable telemetry circuits known in the art that may be used with the present invention for the telemetry circuit 44. See, e.g., U.S. Pat. No. 4,847,617, incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel. Throughout the discussion that follows, reference may be made to "atrial channel activity" or "ventricular channel activity." Atrial channel activity comprises either the sensing of a P-wave by the sense amplifier 22, or the generating of an A-pulse by the A-pulse generator 18. Similarly, ventricular channel activity comprises either the sensing of an R-wave by the sense amplifier 24 or the generation of a V-pulse by the V-pulse generator 20.

In some pacemakers that implement the present invention, the pacemaker 10 may further include one or more physiological sensors 52 that is/are connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors, such as sensors that sense the oxygen content of blood, respiration rate, pH of blood, body position, and the like, may also be used in lieu of, or in addition to, an activity sensor. The type of sensor, if any, used is not critical to the present invention. Any sensor or combination of sensors capable of sensing some physiological parameter relatable to the rate at which the heart should be beating can be used. A pacemaker using such sensors is commonly referred to as a "rate-responsive" pacemaker because it adjusts the pacing rate (escape interval) of the pacer in a manner that tracks the physiological needs of the patient.

Figure 2:
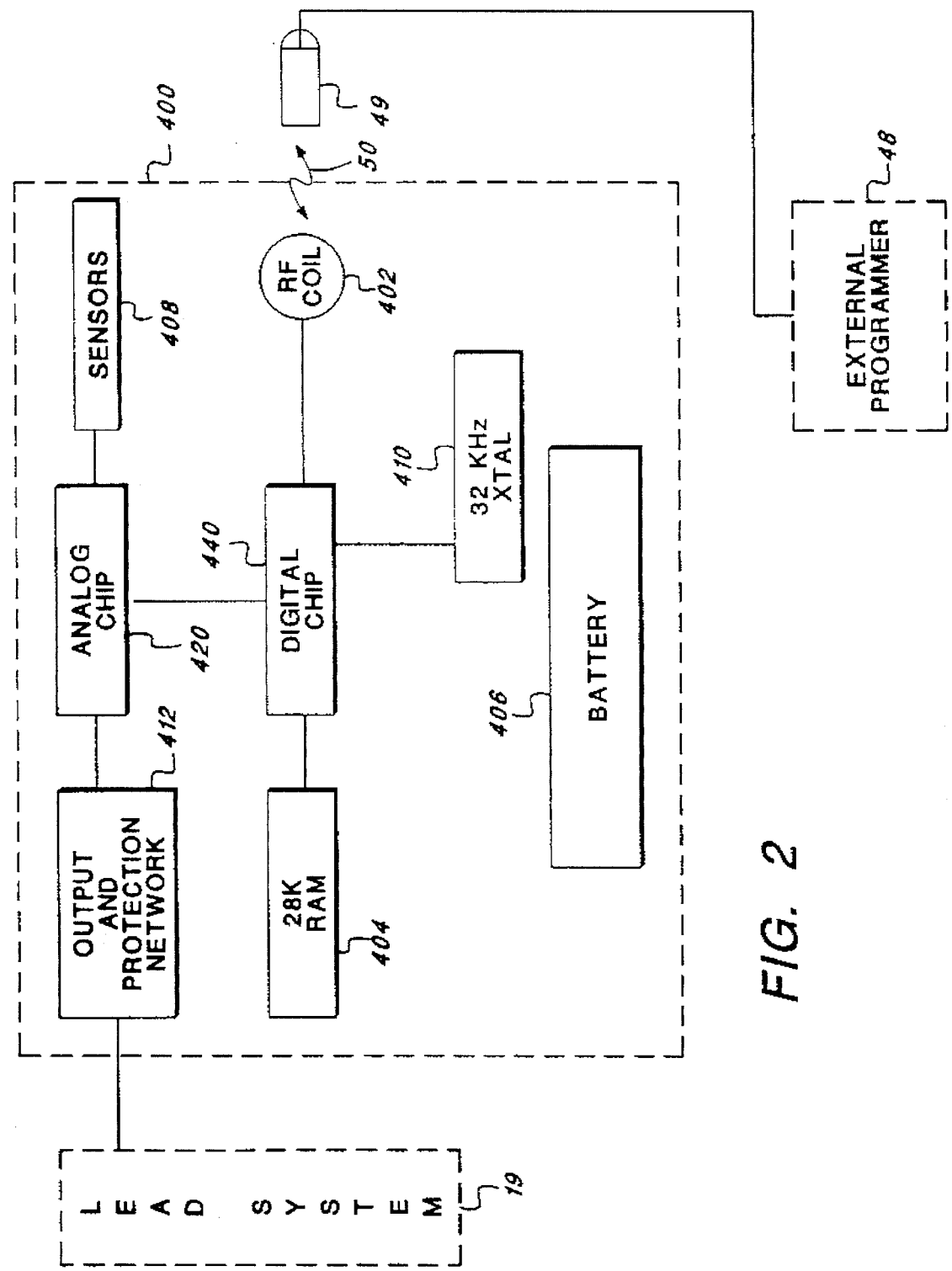
FIG. 2 is a block diagram of a pacing system that depicts the main hardware components of an implantable pacemaker.

Referring next to FIG. 2, there is shown a preferred configuration for a pacing system that implements the present invention. The system includes the external programmer 48, the implantable pacemaker 10, and the lead system 19. The lead system 19 includes conventional atrial and ventricular leads and electrodes, as described previously. The lead system 19 may also include an oxygen sensor lead, which lead contains an LED-detector assembly used to measure the oxygen content of the blood. Such a lead is described, e.g, in U.S. Pat. No. 4,815,469, incorporated herein by reference.

The external programmer 48 includes a telemetry head 49 that is positioned proximate the implantable pacemaker 10 whenever the communication link 50 is to be established between the pacemaker 10 and the external programmer 48. The external programmer may be of conventional design, as described, e.g., in U.S. Pat. No. 4,809,697, incorporated herein by reference.

The components of the pacemaker 10 are housed within a suitable sealed case or housing 400 (which case or housing is represented in FIG. 2 by the dashed line 400). The case 400 is preferably a titanium metal case. The components within the case 400 include an RF coil 402, a memory chip 404, a battery 406, one or more sensors in a sensor circuit 408, a crystal 410, an output/protection network 412, an analog chip 420 and a digital chip 440.

The battery 406, which is by volume the largest component within the pacemaker 10, may be of conventional design, and is a lithium battery that provides operating power to all of the electronic circuits within the pacemaker. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 is a low-power static random access memory (RAM) chip wherein the operating parameters, e.g., control variables, of the pacemaker may be stored, and wherein sensed data may be stored, as required. The analog chip.420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412, which network includes output capacitors, appropriate feed-through connectors to allow electrical connection through the hermetically sealed case, and the like, as are commonly used in implantable medical devices.

Figure 3:
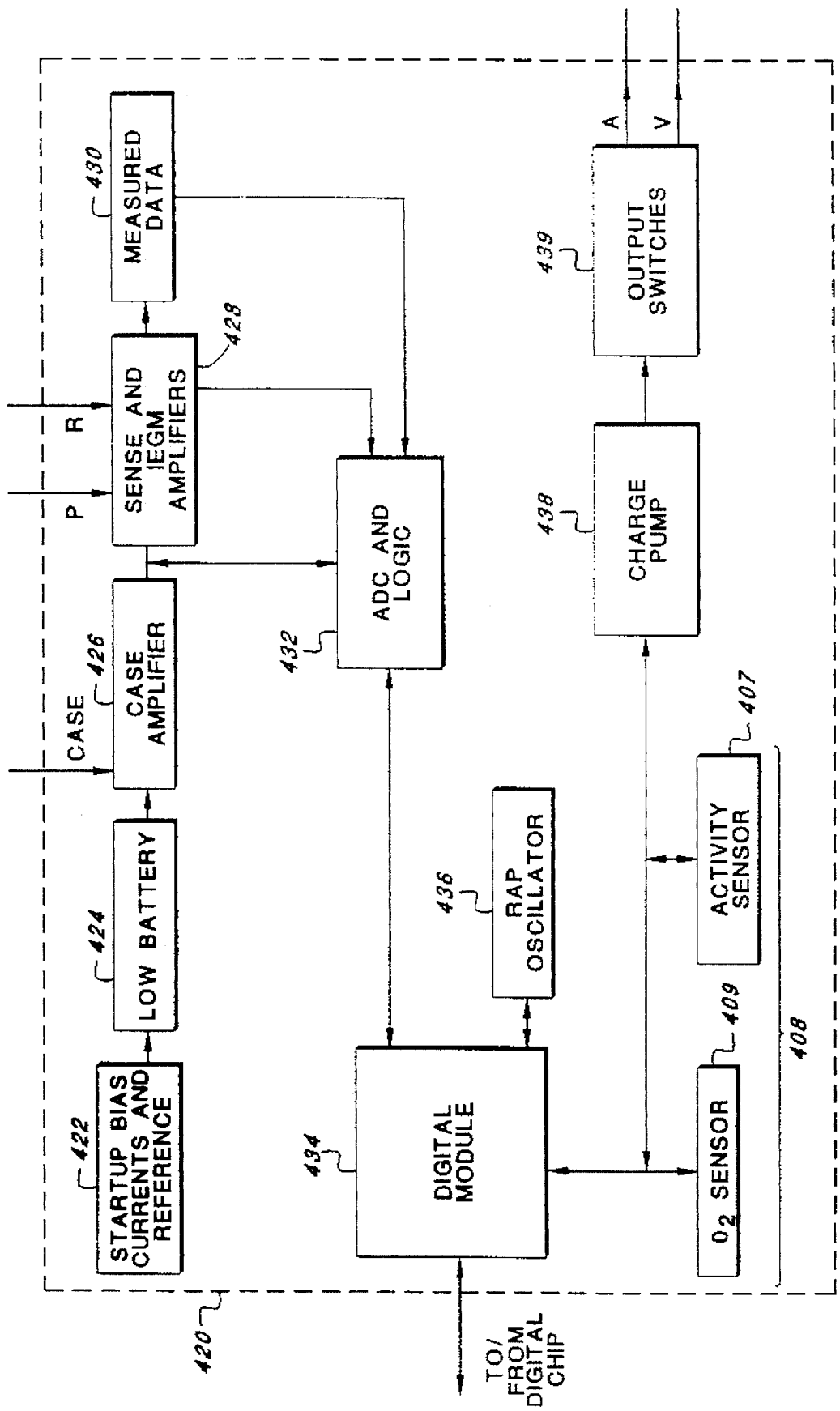
FIG. 3 is a block diagram of the analog chip portion of the pacemaker of FIG. 2.

Referring next to FIG. 3, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The module 428 includes the P-wave amplifier 22 and the R-wave amplifier 24, described above in FIG. 1. A measured data module 430 measures the battery voltage and current and other analog parameters of the pacing system. An ADC and Logic module 432 includes an analog-to-digital converter and timing logic that are used to convert the analog signals of the pacemaker in to 8-bit digital words. These digital words are then passed to a digital module 434, which module is used to generate all the basic timing and bus control functions as data is passed back and forth between the analog chip 420 and the digital chip 440.

Still referring to FIG. 3, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408. The sensor network 408 includes appropriate sensors for sensing activity and other parameters. For example, an 02 sensor circuit 409 may be used in conjunction with the oxygen sensor lead, when used, to measure blood oxygen of the patient. An activity sensor 408 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 4:
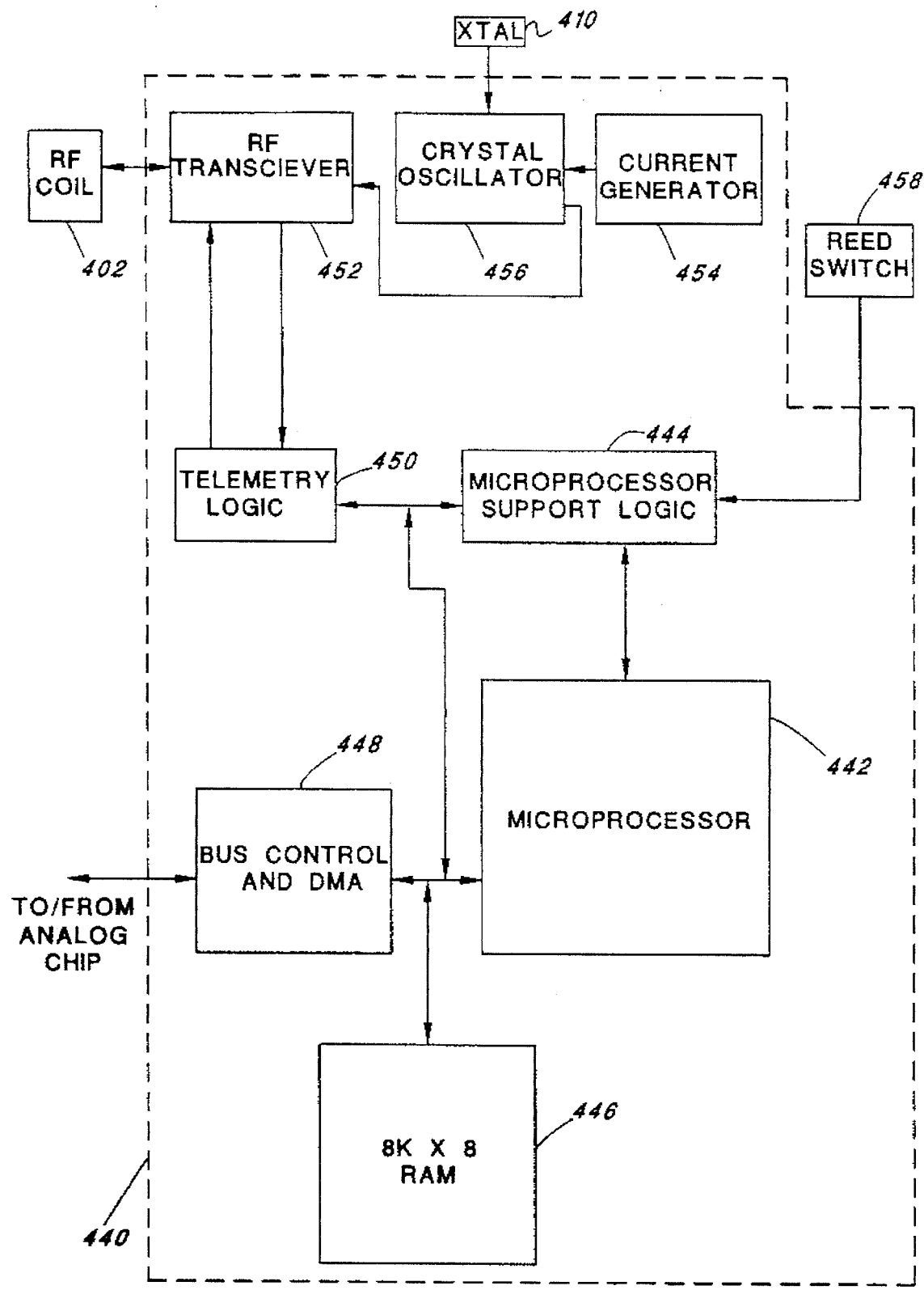
FIG. 4 is a block diagram of the digital chip portion of the pacemaker of FIG. 2, and illustrates the use of a microprocessor to control the operation of the pacemaker.

Turning next to FIG. 4, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit) and 8 K of static RAM. In addition, an 8K by 8K RAM 446 is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide DMA timing and control of data transfer with the analog chip 420, including timing and control of the analog-to-digital converter 432 (FIG. 10) and telemetry data. Telemetry channel logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 4). A crystal oscillator circuit 456, in conjunction with the crystal 410 (external to the digital chip 440) provides the crystal time base of the pacemaker system. A current generator 454 provides the bias currents for the digital chip. A reed switch circuit 458 detects the presence of a magnetic field, which magnetic field is present whenever the telemetry head 49 is in place on the patient's skin above the location where the pacemaker is implanted.

The pacemaker circuitry described in connection with FIGS. 2–4 above provides the basic functions of the pacemaker described in connection with FIG. 1, plus other pacing/sensing functions as are known in the art. For purposes of the present invention, the pacemaker circuitry of FIGS. 2–4 sets the basic timing of the pacing interval, including setting a PV interval, a VA interval, and a MMRI. The circuitry also provides for sensing or detecting natural ventricular events (R-waves) and/or natural atrial events (P-waves), and for measuring the time interval between sensed atrial events, i.e., a P-to-P interval, and paced ventricular events, e.g., a V-to-V interval.

Figure 5:
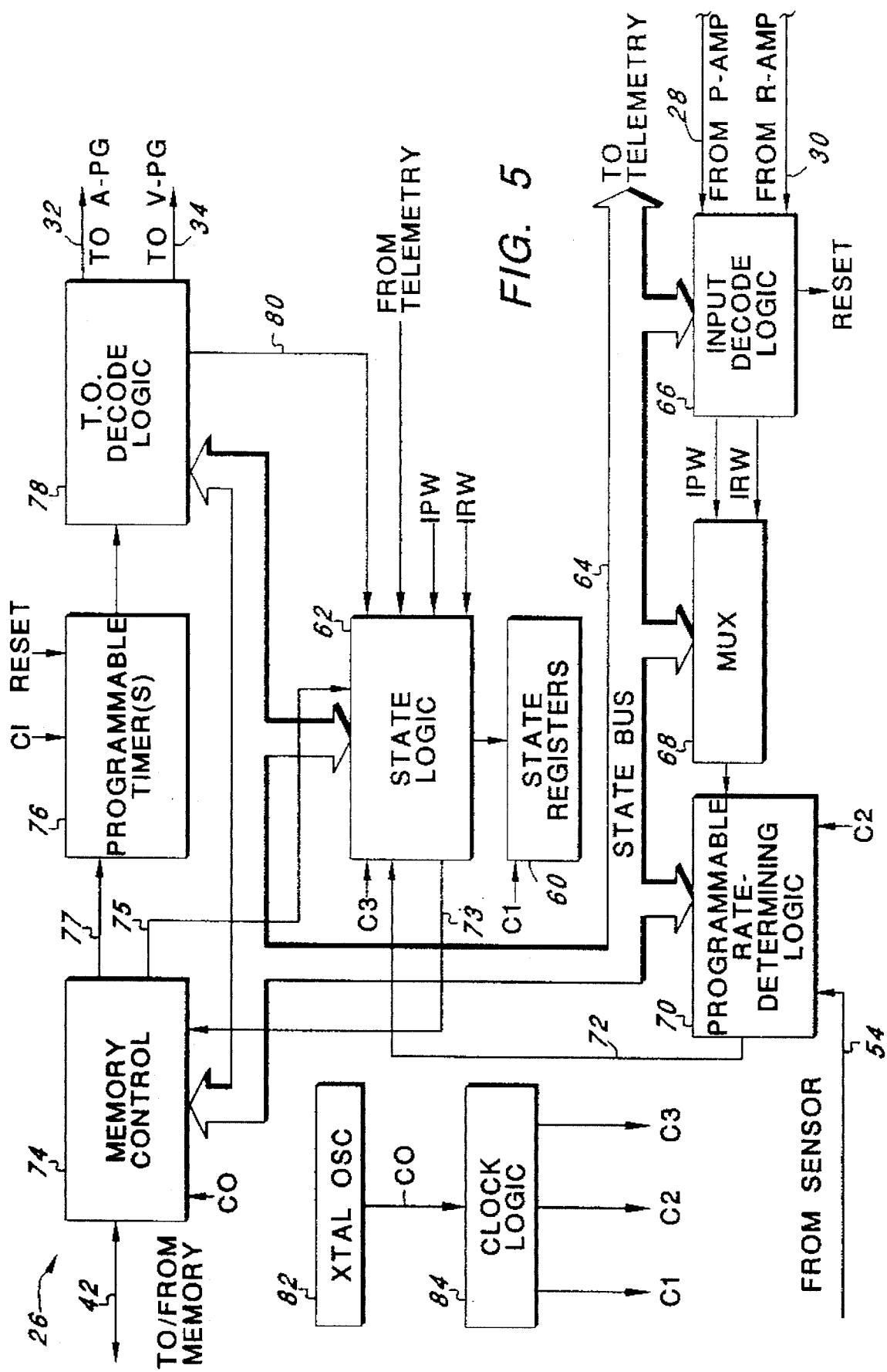
FIG. 5 is a block diagram of a state-machine based dual-chamber pacemaker of a type that could be used to implement the present invention.

Referring next to FIG. 5, a block diagram of an alternative embodiment of the control circuit or system 26 of the pacer 10 (FIG. 1) is illustrated. It is noted that in addition to the embodiment of the invention illustrated above in FIGS. 2–4, or below in FIG. 5, that still other embodiments of a control system 26 may be utilized. The embodiment described above in FIGS. 2–4 shows a control system and pacemaker configuration that is based on a microprocessor. Another representative microprocessor-based system is described, for example, in U.S. Pat. No. 4,940,052, entitled "Microprocessor Controlled Rate-Responsive Pacemaker Having Automatic Threshold Adjustment," incorporated herein by reference.

The control system shown in FIG. 5 is based on a state machine wherein a set of state registers 60 define the particular state of the pacer at any instant in time. As is known in the art, state machines may be realized using dedicated hardware logic circuits, or a suitable processor (programmed-controlled circuit) to simulate such dedicated hardware logic circuits. However implemented, the results are the same—the state of the pacer is defined at any instant of time by the pacemaker logic and sensed events which transpire or fail to transpire, such as the sensing of an R-wave, or the timing out of a timer. A complete description of FIG. 5, including basic state machine operation, may be found in the patent applications that have been incorporated herein by reference. The various circuits of the control system 26 of FIG. 5, or simulated equivalents thereof, may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their inter-relationship are more thoroughly described; and U.S. Pat. No. 4,944,298 wherein an atrial-rate based programmable pacemaker is described, including a thorough description of the operation of the state logic used to control such a pacemaker. The '555, '980 and '298 patents are also incorporated herein by reference.

The details of the control system 26, whether based on a microprocessor, state machine, or other type of control devices, or simulated control devices, are not critical to an understanding or implementation of the present invention, and hence are not presented herein. Such details may be found in the referenced applications and patents, if desired. All that is needed for purposes of the present invention is that the control system of the pacemaker, in conjunction with other pacemaker circuitry, be capable of the basic pacing functions as described above, including: (a) setting the pacing interval, and the various subintervals that make up the pacing interval, e.g., the PV interval (PVI), the PVARP, the Wenkebach interval (WI), the atrial lock interval (ALI) and the P-wave tracking interval (also referred to as the "P-track" interval); (b) keeping track of the number of P-waves or other cardiac events that occur, and when such events occur relative to the various defined timed intervals; (c) generating (when used) a free-running maximum mean rate interval (MMRI); (d) storing or latching the occurrence of certain events for later reference or processing; and (e) carrying out whatever processing of these stored or latched events is required, e.g., starting the PVI, inhibiting the generation of a V-pulse, issuing a phantom P-wave to start a PVI, etc., as described more fully below.

Thus, given a pacemaker constructed as described above in connection with FIGS. 1–5, or an equivalent pacemaker, the present invention relates primarily to controlling the upper rate performance of the pacemaker, and more particularly to controlling the upper rate performance so that the ventricular activity of the heart remains synchronized with (i.e., "locked" to) the atrial activity for a larger percentage of the time. Such atrial-locked pacing advantageously improves cardiac output at the upper rates of the pacemaker.

Figure 6:
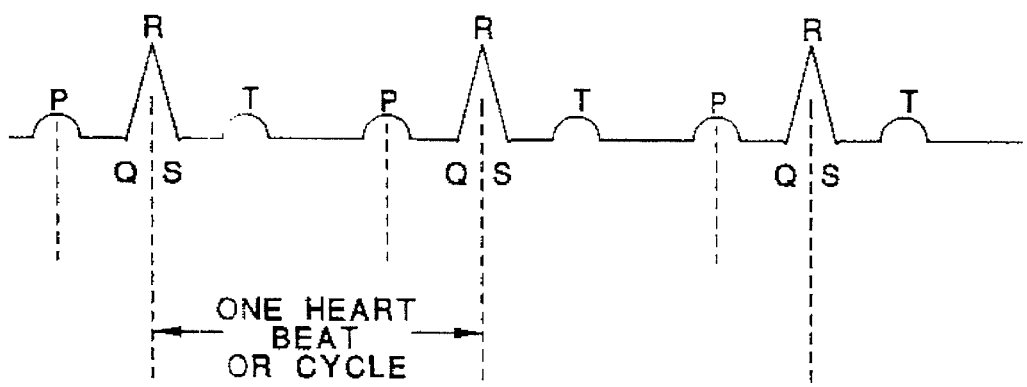
FIG. 6 illustrates P-waves and R-waves associated with a basic cardiac cycle.

To better understand the present invention, reference is momentarily made to FIG. 6, where there is shown a typical ECG- or EGM-type waveform illustrating the normal A-V synchrony or rhythm of a heart. Beginning at the left, there is shown a P-wave representing the electrical activity coincident with the depolarization of the atria of the heart. Depolarization of the atria is accompanied by contraction of the atria, which contraction pushes blood from the atria into the ventricles. A short time subsequent to the generation of the P-wave, the QRS complex appears, representing the depolarization of the ventricles. The time period between the P-wave and the QRS wave (generally referred to as simply the "R-wave") is a very important time interval in the operation of the heart because it represents the time needed for the blood to flow from the atria into the ventricles. The R-wave is followed by a T-wave, which represents the electrical activity associated with the repolarization of the ventricles. Typically, one heartbeat or heart cycle is measured as the time interval between succeeding R-waves simply because the R-wave is generally the easiest of the waves to identify and measure. A heartbeat may, of course, be measured relative to any point within the heart cycle, such as between succeeding P-waves, or T-waves.

The important point for purposes of the present application is to recognize that a certain A-V synchrony must occur if the heart is to function efficiently as a pump, i.e., if a sufficient amount of blood is to be pushed out of the ventricles with each contraction. More particularly, the depolarization of the atria, represented by the P-wave, must be followed a short time thereafter by the depolarization of the ventricles, represented by the R-wave, in order to maintain an adequate stroke volume. After a sufficient delay, the atria must again depolarize, followed by the depolarization of the ventricles. When the depolarization of the atria or ventricles do not occur naturally, then a pacemaker may be employed to provide stimulation pulses to these respective heart chambers, in order to trigger the required depolarization/contraction at the appropriate time periods of the heart cycle. The pacemaker, like the natural depolarizations, attempts to maintain the basic P-V time interval between atrial depolarization and ventricular depolarization so as to preserve the AV synchrony needed to optimize cardiac output. To this end, P-waves may be "tracked" by the pacemaker, meaning that for every sensed P-wave, a V-pulse is generated one PV interval thereafter (unless an R-wave occurs before the PV interval has timed out).

Generally, when utilizing a pacemaker at its upper or higher pacing rates, a P-V sequence (a P-wave followed by a V-pulse) occurs at a rate that is limited by the maximum tracking rate (MTR) of the pacemaker. The MTR is generally a programmable parameter set by the cardiologist at the time the pacemaker is implanted. A typical MTR may lie within the range of 100 to 170, e.g., 150 bpm. In a pacemaker that tracts P-waves, the MTR interval (MTRI) defines the shortest time interval that the pacemaker allows between acting upon sensed atrial events, and in so doing, limits the ventricular pacing rate (i.e, the rate at which V-pulses may be generated. This is usually accomplished as illustrated in the timing waveform diagram of FIG. 7.

Figure 7:
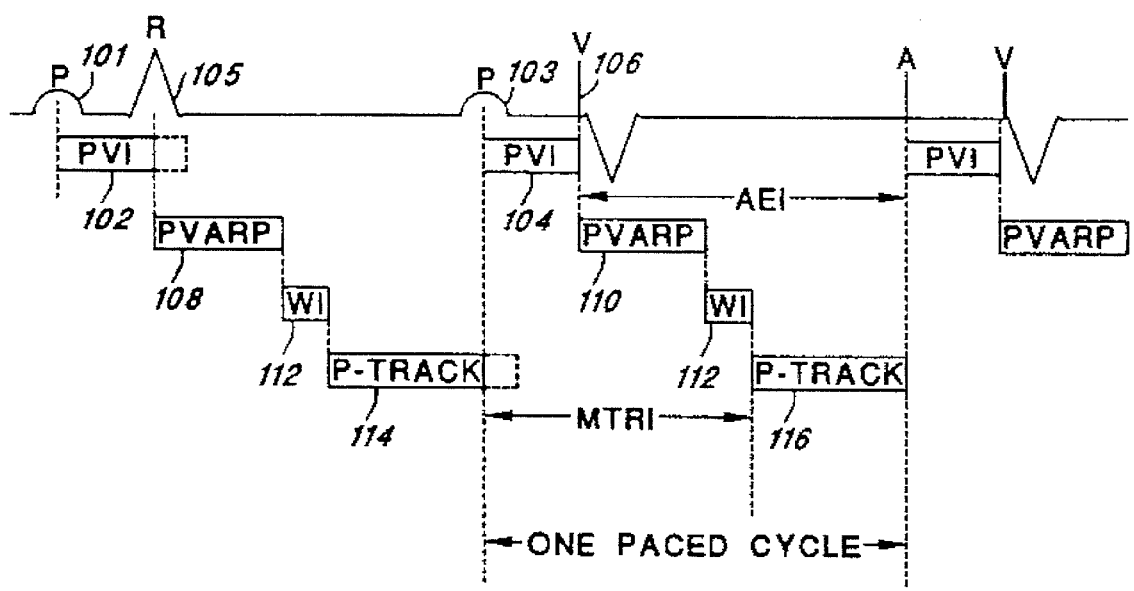
FIG. 7 is a timing waveform diagram that depicts the various ventricular-based timing intervals commonly used to limit the upper rate performance of a pacemaker.

In FIG. 7, a PV interval, or PVI, is initiated by the pacemaker timing circuits upon the sensing of a P-wave. Thus, as seen in FIG. 7, a first PVI 102 begins after sensing P-wave 101, and a second PVI 104 begins after sensing P-wave 103. If natural ventricular activity, i.e., an R-wave 105 is sensed prior to the timing out of the PVI, then the PVI is cut short or reset upon the occurrence of the R-wave. Such a situation is depicted in FIG. 7 for the PVI 102 and the R-wave 105. If no ventricular activity occurs, the PVI times out, and a V-pulse is generated, as depicted in FIG. 7 for the PVI 104 and the V-pulse 106.

The occurrence of ventricular activity, whether an R-wave or a V-pulse, starts the post ventricular atrial refractory period (PVARP). A PVARP 108 is shown in FIG. 7 following the shortened PVI 102, and another PVARP 110 is shown following the timed out PVI 104. During the timing out of the PVARP, P-waves are not sensed (and even if they are sensed, e.g., during a latter portion of PVARP, they are not tracked). Following the PVARP, a Wenkebach interval (WI) 112 begins. During the WI, P-waves are tracked but delayed, i.e., any P-waves that are sensed are not acted upon until WI ends. This results in a lengthening of the P-to-V period, which may produce the electrophysiologic problems previously mentioned, i.e., retrograde conduction may be enhanced, thereby increasing the susceptibility of the heart to a pacemaker mediated tachycardia (PMT). The pacemaker uses the combined time interval defined by the sum of the PVI, PVARP and WI to set the MTRI. Because the PVI and PVARP are more or less fixed, the WI is thus changed, as the MTR is programmed, in order to define the appropriate MTRI corresponding to the programmed MTR.

Following the WI, a P-track interval 114 or 116 begins. During the P-track interval, P-waves are tracked in conventional manner. That is, any P-wave sensed during the P-track interval (such as the P-wave 103, which occurs during the first P-track interval 114) causes the P-track interval to be reset, and the next pacing cycle to begin, i.e., a sensed P-wave causes the next PVI to begin, followed by PVARP, etc. Note, the time period beginning with a ventricular event, e.g., the V-pulse 106, to the end of the following P-track interval, is sometimes referred to as the atrial escape interval, or AEI. Note, also, that once PVARP begins, following a ventricular event (either an R-wave or a V-pulse), the other time intervals (WI and P-track) are timed relative to PVARP. For this reason, the use of time intervals as illustrated in FIG. 7 to provide stimulation pulses is commonly referred to as a ventricular-based pacing.

In summary, as seen in FIG. 7, the conventional ventricular-based technique used to control the upper rate performance of a pacemaker is to employ an MTRI, comprised of the sum of the PVI, PVARP and WI. P-waves are not tracked during PVI and PVARP, but are tracked during the WI (but delayed) and the P-track interval. As P-waves occur sooner and sooner in the P-track interval, the pacing rate (i.e., the rate at which V-pulses are generated following each tracked P-wave) increases faster and faster, until the P-waves occur at the very beginning of each P-track interval, at which point the rate at which P-waves may be tracked is limited by the MTR. (It is possible, of course, for P-waves to occur during the WI (in which case they are tracked but delayed) or during the PVARP (in which case they are not tracked). For example, at certain P-wave rates it is possible for every other P-wave to be sensed and tracked during the P-track interval, with the remaining P-waves falling into, and hence being blocked by, PVARP, a condition known as 2:1 block. During 2:1 block, a V-pulse is thus generated at a rate that is only one-half the P-wave rate.

Figure 8:
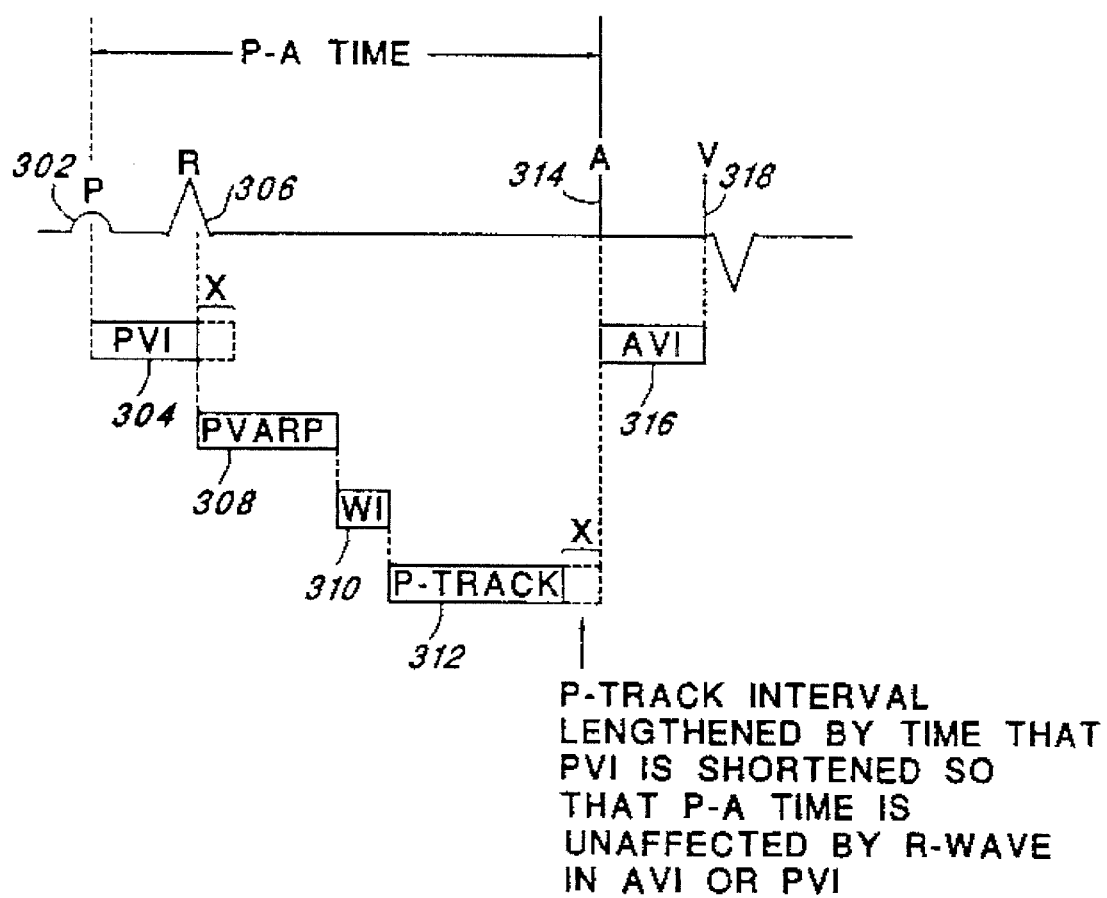
FIG. 8 is a timing waveform diagram as in FIG. 7, but depicts atrial-based timing instead of ventricular-based timing.

As previously indicated, that which is shown in FIG. 7, relates to ventricular-based timing. It should be noted that is also possible to operate a pacemaker based on atrial-based timing, as illustrated in FIG. 8. The modified P-wave tracking modes of the present invention may be implemented using either a ventricular-based timing system, or an atrial-based timing system, even though much of the description which follows (e.g., FIGS. 9-1 through 10-3) is based on a ventricular-based timing system.

In an atrial-based timing system, as seen in FIG. 8, a PVI 304 begins following a sensed P-wave 302. However, before the PVI times out, an R-wave 306 occurs. This R-wave cuts short the PVI 304, and causes PVARP 308 to begin. Following PVARP 308, a WI 310 starts, followed by a P-track interval 312. However, unlike the ventricular-based timing approach of FIG. 7, when the PVI 304 is shortened when using an atrial-based timing system as shown in FIG. 8, the P-track interval 312 is extended or lengthened by the amount of time that the PVI 304 is shortened. At the end of the lengthened P-track interval, assuming that no P-waves have been sensed, an A-pulse 314 is generated. The A-pulse 314 starts an AVI 316, following which a V-pulse 318 is generated (assuming no R-wave occurs during the AVI 316). In this fashion, the PVI or AVI is shortened whenever an R-wave occurs before the end of the PVI or AVI, but the P-track interval is lengthened by the same amount, thereby leaving the overall P-to-A time (i.e., the paced cardiac cycle period, or the time from the P-wave 302 to the A-pulse 314 in FIG. 8) unaffected by the occurrence of the R-wave during the PVI or the AVI.

Figures 3, 9:
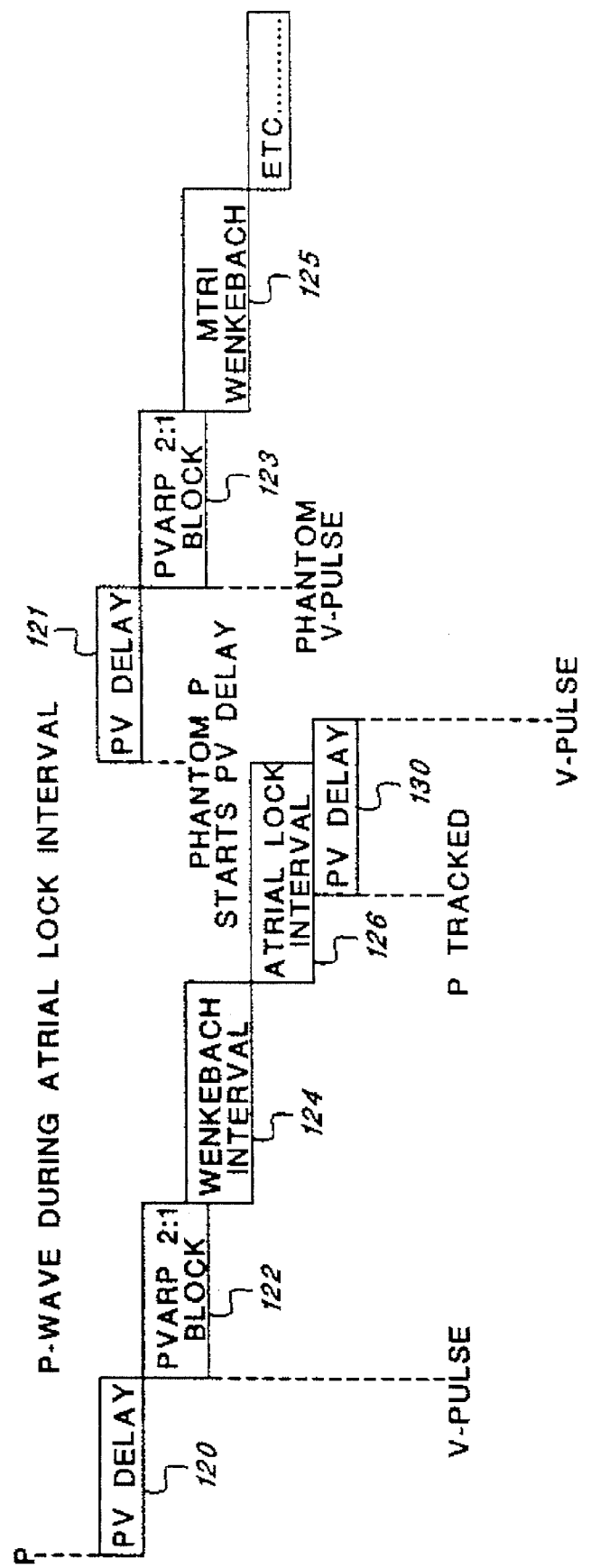

Referring next to FIG. 9-1, there is shown a timing diagram that illustrates the various timing intervals used to define a pacing interval in accordance with a first variation of a first embodiment of a modified P-wave tracking mode of the present invention. As seen in FIG. 9-1, the intervals thus used include a PV delay 120, a PVARP 122, a Wenkebach Interval (WI) 124, an Atrial Lock Interval (ALI) 126 and a P-track interval 128. A comparison of FIG. 9-1 with FIG. 7 reveals that FIG. 9-1 includes the addition of the ALI 126 between the WI 124 and the P-track interval 128.

To understand how the inclusion of the ALI 126 affects the pacemaker operation, it is helpful to review how the pacemaker responds to the occurrence of a P-wave in each of the sub-intervals shown in FIG. 9-1. That is, it is helpful to understand what happens when a P-wave occurs in each of the intervals shown in FIG. 9-1.

Should a P-wave occur during either the PV delay 120 or the PVARP 122, such event is not tracked. That is, a P-wave occurring during either the PV delay or PVARP is ignored by the pacemaker circuits. This is the normal convention, and causes a 2:1 or higher block at high atrial rates.

If a P-wave occurs during the Wenkebach Interval (WI) 124, then a P-wave is latched and a phantom P-wave is generated at the end of the ALI 126, as shown in FIG. 9-2. The phantom P-wave at the end of the ALI causes a PV delay 121 to begin at the end of the ALI just as if a P-wave had occurred at the end of the ALI. Hence, the effect of using a phantom P-wave as shown in FIG. 9-2 is to treat any P-wave that occurs during the WI as though it occurred at the end of the ALI. Thus, as seen in FIG. 9-2, for every P-wave that occurs during the WI 124, a new PV delay 121 is started at the end of the ALI 126 that follows the WI during which the P-wave occurs. A V-pulse is then provided after the PV delay 121. After the V-pulse, a PVARP 123 is initiated, as is conventional following a V-pulse, followed by a new WI 125, and so on (the cycle of intervals repeats).

FIG. 9-3 illustrates what happens when a P-wave occurs during the ALI 126. As seen in FIG. 9-3, when a P-wave occurs during the ALI 126, such P-wave is tracked by generating an intermediate PV delay 130, following which a V-pulse is generated. Further, at the end of the ALI 126 during which the tracked P-wave occurs, a phantom P-wave is assumed that starts a second PV delay 121. The second PV delay 121 begins a new pacing cycle. That is, following the second PV delay 121, a phantom V-pulse (not a real V-pulse, but only a pulse used for timing purposes) is generated that triggers a new PVARP 123, following which a new WI 125 begins, and so on. Only a phantom V-pulse follows the second PV delay 121, rather than an actual V-pulse, because an actual V-pulse was generated just prior thereto at the conclusion of the intermediate PV delay 130.

Note from FIG. 9-3 that the delivery of the V-pulse at the conclusion of the intermediate PV delay 130 is at an interval shorter than the usual and allows for tracking. P-waves that occur as early in the pacing interval as PVI+PVARP+WI, where PVI is the PV interval (or PV delay). Thus, the maximum instantaneous upper ventricular rate is defined by:

$$\text{Max Instantaneous Upper Rate} = 1/(PVI+PVARP+WI). \quad (1)$$

However, while the max instantaneous ventricular rate is as defined by Eq. (1) above, the invention further limits the maximum mean (or average) rate (MMR) by keeping track of the time out of the ALI 126 and assuming that a phantom P-wave occurs at the time out of the ALI. This phantom P-wave causes a phantom PV delay (the second PV delay 121 shown in FIG. 9-3), following which the PVARP 123 begins. As indicated above, since the V-pulse was already delivered at the conclusion of the intermediate PV delay 130, it is not necessary (nor desirable) to deliver another V-pulse at the conclusion of the phantom PV delay 121. Thus, only a phantom V-pulse is delivered at the timing out of the phantom PV delay 121, causing the next PVARP 123 to begin.

The ALI response shown in FIG. 9-3 produces an average ventricular rate that approaches or remains below the rate defined by:

$$MMR \leq 1/(PVI+PVARP+WI+ALI). \quad (2)$$

Should a P-wave occur during the P-track interval 128, then such P-wave is tracked in conventional manner. That is, if a P-wave occurs during the P-track interval, the PV delay is started, following which a V-pulse is delivered (in the absence of an R-wave occurring prior to the time out of the PV delay), and PVARP is started.

The ALI pacing scheme depicted in FIGS. 9-1 through 9-3 above offers the following significant advantages: (1) 2:1 block exists for high atrial rates; (2) pacemaker Wenkebach is provided (i.e., the MTR takes effect) at a fairly high atrial rate; and (3) P-waves in the ALI are tracked. Significantly, the maximum upper instantaneous ventricular rate may be as high as indicated by Eq. (1) above, yet the average ventricular rate will be limited by Eq. (2) above. Further, if the ALI is set equal to 0 ms (zero), then the system behaves as a typical DDD pacer, i.e., as the P-wave rate increases, there is first P-tracking, then Wenkebach pacing, and then 2:1 block. Also, if the WI is set equal to 0 ms (zero), then the system behaves entirely in the ALI mode. That is, P-waves are tracked all the way up to 2:1 block at a maximum instantaneous rate of 1/(PVI+PVARP), yet the mean rate remains below or approaches 1/(PVI+PVARP+ALI).

A flowchart that depicts the ALI pacing technique illustrated in the timing waveform diagrams of FIGS. 9-1 through 9-3 is described below in connection with FIGS. 13-1 and 13-2.

Figures 3, 10:
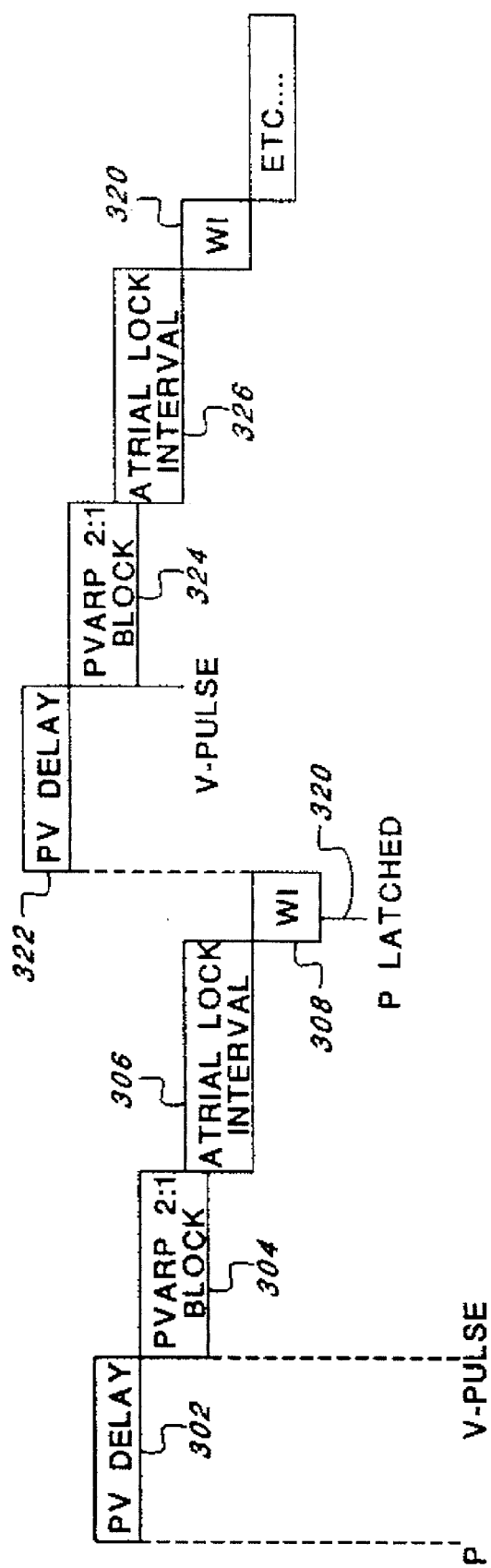

Referring next to FIG. 10-1, there is illustrated the various timing intervals used to define a pacing interval in accordance with a second variation of the first embodiment of the modified P-wave tracking mode of the present invention. As seen in FIG. 10-1, these intervals include a PV delay 302, a PVARP 304, an atrial lock interval (ALI) 306, a Wenkebach interval (WI) 308, and a P-track interval 310. A comparison of FIG. 10-1 with FIG. 9-1 reveals that the position of the ALI and the WI in the sequence of timing intervals has been reversed. That is, in the second variation (FIG. 10-1), the ALI 306 follows the PVARP 304; and then the WI 308 follows the ALI 306. The P-track interval 310 then follows the WI 308.

FIG. 10-2 depicts what happens in the second variation when a P-wave is sensed during the ALI 306. As seen in FIG. 10-2, a P-wave 307 that occurs during the ALI 306 is tracked, causing a phantom P-wave to be generated at the end of the ALI 306. The phantom P-wave triggers an extended PV delay 312, followed by a PVARP 314, followed by another ALI 316, followed by another WI 318, and so on. Meanwhile, the P-wave 307 sensed during the ALI 306 triggers yet another extended PV delay 311, at the conclusion of which a V-pulse 313 is generated and delivered to the heart. Because of the V-pulse 313, there is no V-pulse generated at the conclusion of the second PVARP 314, only a phantom V-pulse 315. The extended PV delay 311 and the extended PV delay 312 are each extended by an amount equal to the WI 308. That is, the total length of the extended PV delays 311 and 312 is equal to the normal PV delay 302 plus the WI 308.

Turning next to FIG. 10-3, there is shown an illustration of the second variation of the first embodiment of the invention when a P-wave occurs during the Wenkebach interval. As seen in FIG. 10-3, a P-wave 320 that occurs during the WI 308 is latched, causing a PV delay 322 to begin at the conclusion of the WI 308. A V-pulse 323 is then generated at the conclusion of the PV delay 322. The V-pulse 323, in turn, causes another PVARP 324 to be generated, followed by another ALI 326, followed by another WI 328, etc.

A study of FIGS. 10-1 through 10-3 reveals that the second variation of the first embodiment of the invention there illustrated provides some prolongation of the AVI (or PVI), up to a limit, and then it locks at that limit (with no further prolongation). The mean ventricular rate thus achieved approaches the programmed MMRI.

Yet a third variation of the first embodiment of the modified P-wave tracking mode of the present invention comprises starting the PVI 121 at the end of the WI 124, rather than at the end of the ALI 126, as in the first variation (FIGS. 9-2 and 9-3). Such a variation results in a faster Wenkebach rate, which could be useful for certain patients.

Figure 11:
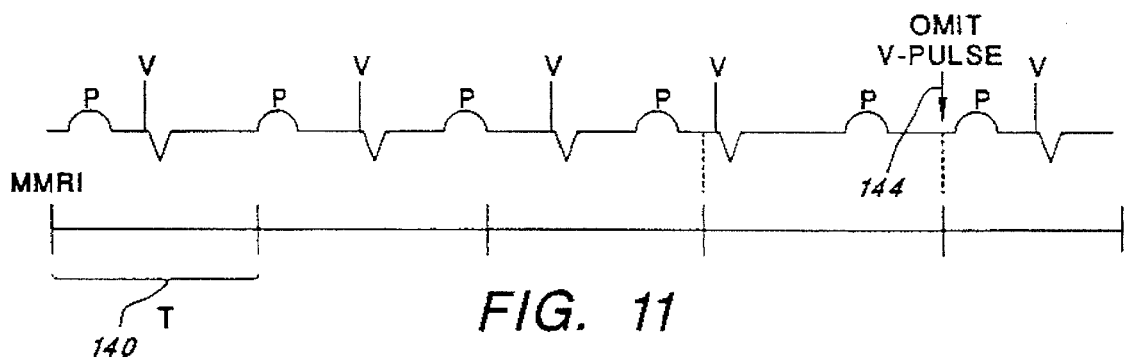
FIG. 11 is a timing diagram that depicts the use of a free-running maximum mean rate interval (MMRI) in accordance with a second modified P-wave tracking mode of the invention.
Figure 12:
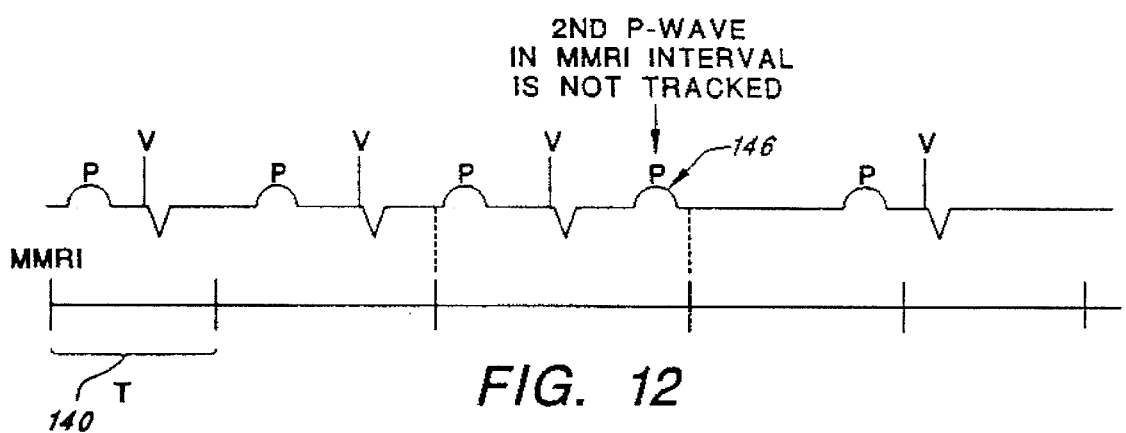
FIG. 12 is a timing diagram that shows a variation of the free-running MMRI approach shown in FIG. 11.

Referring next to FIGS. 11 and 12, additional timing diagrams are shown that depict two MMRI-free-running techniques used in accordance with a second modified P-wave tracking mode of the invention. In such mode, a sequence of MMRI's 140, having, e.g., a period T of 300–600 ms, is generated that runs asynchronously relative to any atrial or ventricular events. That is, the MMRI runs free, repeating itself over and over, at a rate of, e.g., 100–200 bpm. Either of two techniques may be used to track P-waves in accordance with the free-running MTRI mode. In a first technique, shown in FIG. 11, the pacemaker generates a V-pulse only if no prior ventricular activity (R-wave or V-pulse) has occurred during the current MMRI. Thus, in accordance with this first technique, the pacemaker circuits monitor the number of ventricular events that occur during each MMRI. If a V-pulse is to be generated, e.g., at the conclusion of a PV interval, but the generation of such V-pulse would represent the second ventricular activity of the current MMRI, then such V-pulse is inhibited. For example, in FIG. 11, the fourth complete MMRI shown has a first V-pulse 142 that falls near the beginning of the MMRI. Hence, at an upper ventricular rate, a second V-pulse that would otherwise occur near the end of the MMRI, at 144, is inhibited. At the upper rate limit, such action, on average, results in a ventricular rate that is the same as the MMR.

In a second technique, shown in FIG. 12, only the first P-wave of a given MMRI is tracked. A "tracked" P-wave is one that triggers a PV interval, at the conclusion of which a V-pulse is generated if an R-wave has not first occurred. Thus, as seen in FIG. 12, should a second P-wave 146 occur during the given MMRI, such P-wave is ignored, no PV interval is started, and no V-pulse can result. At the upper rate limit, such action (of only tracking one P-wave per MMRI) results, on average, in a ventricular rate that is the same as the MMR.

Thus, it is seen that both the technique shown in FIG. 11 (of only allowing one V-pulse per MMRI), or the technique shown in FIG. 12 (of only tracking one P-wave per MMRI), results is a ventricular rate that, on average, is the same as the maximum mean rate, MMR. The advantages of the MMRI-free-running technique shown in the timing waveform diagrams of FIGS. 11 and 12 are: (1) the simplicity of its implementation; and (2) the achievement of an average ventricular rate equal to MMR for all atrial rates greater than MMR but less than the 2:1 blocking rate (or less than the Wenkebach rate, if employed). Advantageously, the MMRI can be generated using any type of free running oscillator, implemented with hardware and/or software. Monitoring the number of cardiac events that occur during each MMRI then becomes a simple logic circuit which may be implemented using conventional hardware and/or software techniques following the method detailed in the flowcharts of FIG. 14 (corresponding to FIG. 11) or FIG. 15 (corresponding to FIG. 12), or equivalent methods.

The results depicted in FIGS. 9-1 through 10-3 relating to ALI pacing, and to FIGS. 11-12 for MMRI free-running pacing (which is, as noted, also a form of ALI pacing), or any of their variations, may be realized using numerous methods, types of pacemakers, and circuitry. One representative method by which the desired results for some of the variations described above (e.g., the variation shown in FIGS. 9-1 through 9-3, or the variations shown in FIGS. 11 and 12) may be achieved is generally shown below in the flowcharts of FIGS. 13-1, 13-2, 14 and 15. The other variations described above may likewise be achieved using similar methods and techniques. Any type of pacemaker, whether a microprocessor-based pacemaker, a state machine pacemaker, or other pacemaker employing a configurable control system, may be configured to operate in the manner shown in the below flowcharts, or equivalent methods, in order to achieve the desired results described above in connection with FIGS. 9-1 through FIG. 12.

Figures 1, 13:
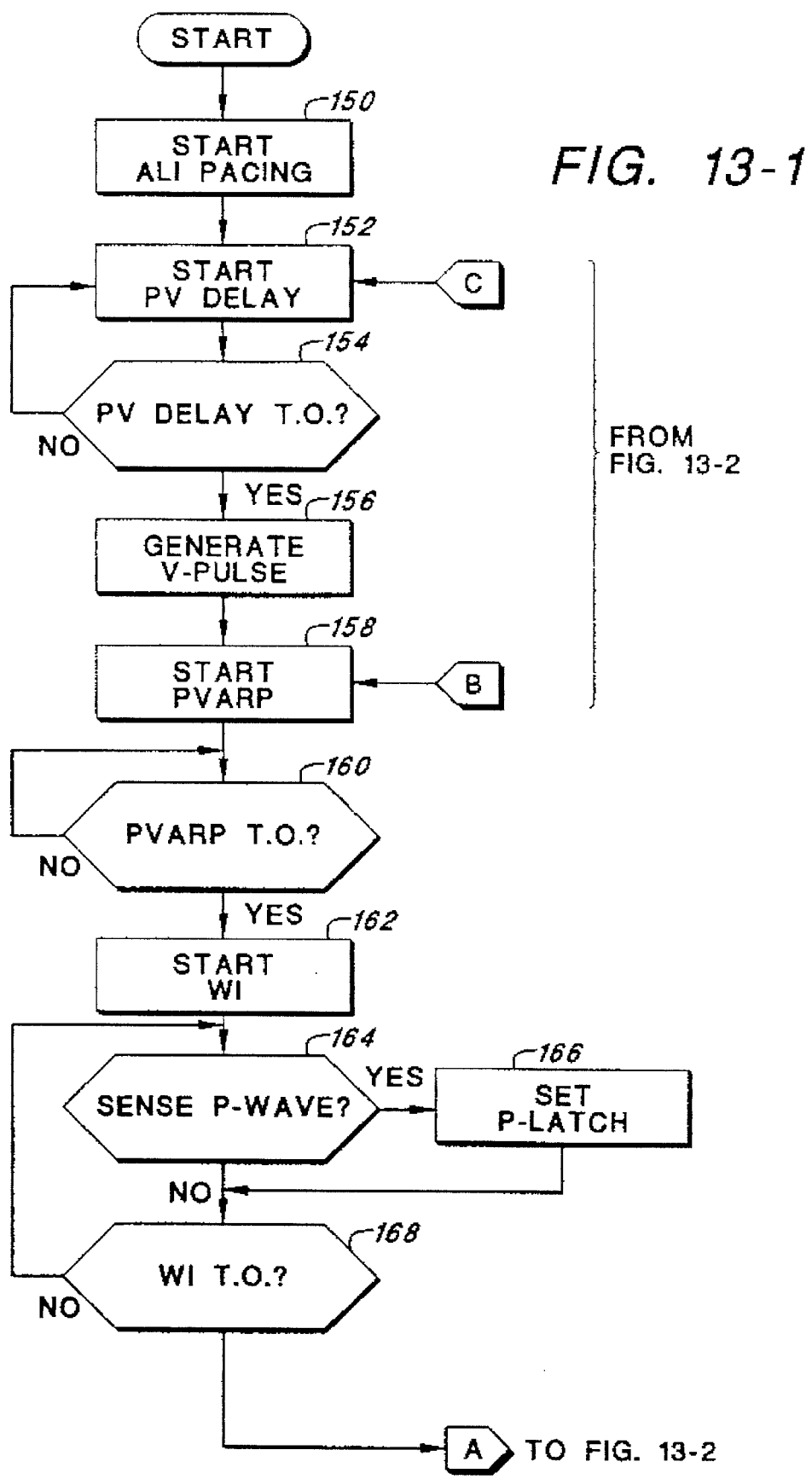
Figures 2, 13:
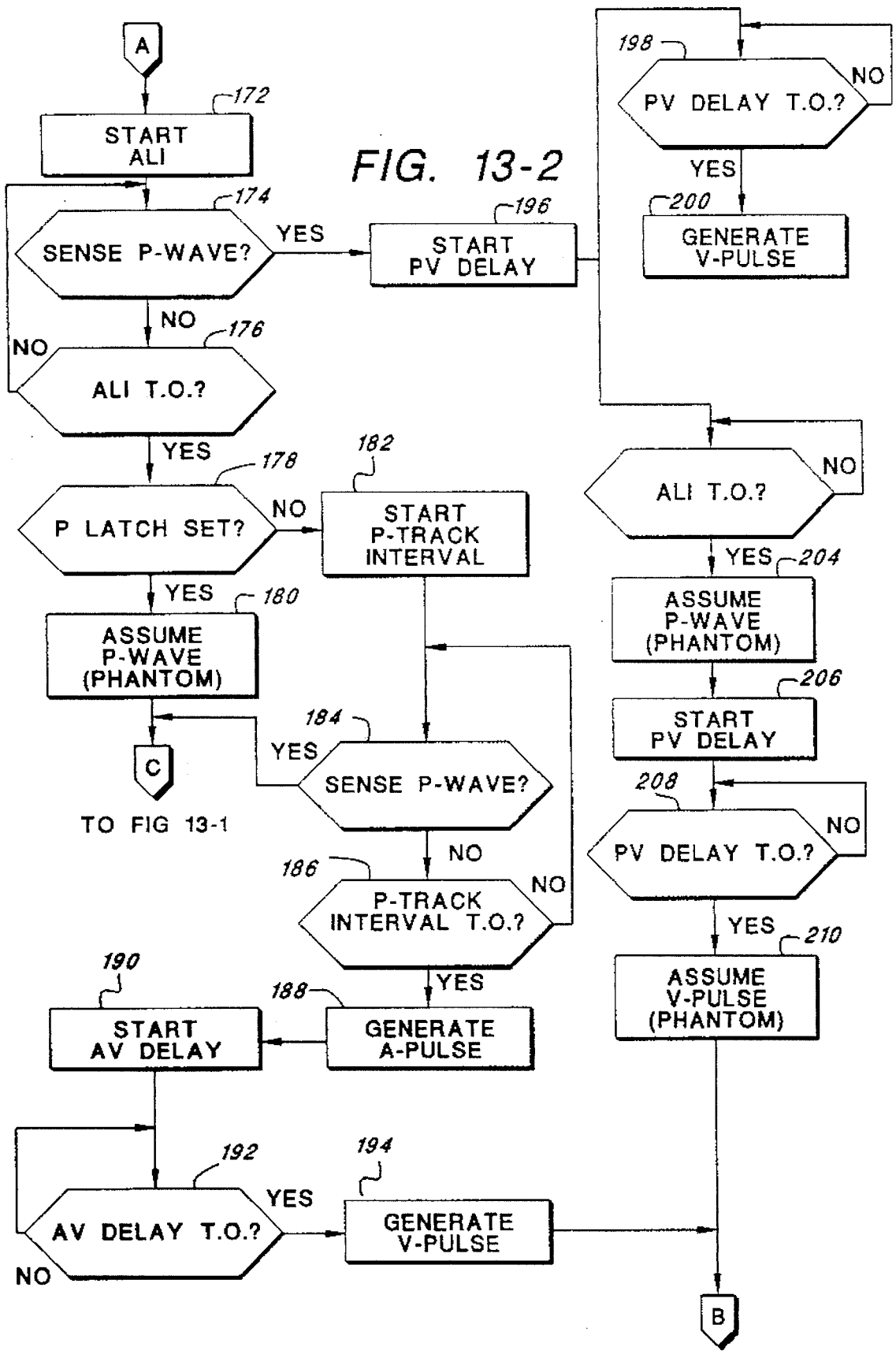

Turning then to the flowcharts of FIGS. 13-1 and 13-2, a preferred method for carrying out the ALI pacing technique described above in connection with FIGS. 8-10 is detailed. It is noted that FIGS. 13-1 and 13-2 include different portions of the same flowchart with appropriate connection blocks "A", "B" and "C" being used to interconnect the portions of the flowchart included in FIG. 13-1 with the portions of the flowchart included in FIG. 13-2.

As seen in FIGS. 13-1 and 13-2, once ALI pacing begins (block 150), the PV delay is started (block 152). When the PV delay times out ("T.O.")(block 154), then a V-pulse is generated (block 156). (It is noted, not shown in FIG. 13-1, that if an R-wave is sensed before the PV delay times out, then no V-pulse will be generated. If an R-wave is sensed, the pacer becomes inhibited in both chambers and no pacing stimuli are delivered.) After the V-pulse is generated, the PVARP begins (block 158). When the PVARP times out (block 160), then the WI begins (block 162). Should a P-wave be sensed (YES branch of block 164) before the WI times out (block 168), then a P Latch is set (block 166).

Once the ALI times out (YES branch of block 168) the ALI starts (block 172, FIG. 13-2). If the ALI times out without sensing a P-wave (block 176), and if the P Latch is set (YES branch of block 178), then a phantom P-wave is assumed (block 180). Such phantom P-wave causes the PV delay to again start (block 152, FIG. 13-1), following which a V-pulse is generated (block 156). If, after the ALI times out, the P Latch is not set (NO branch of block 178, FIG. 13-2), then the P-track interval begins (block 182). Should a P-wave be sensed (block 184) before the P-track interval times out, such P-wave is tracked in conventional manner, i.e., the PV delay again starts (block 152), following which a V-pulse is generated (block 156), PVARP starts (block 158), and the process continues as previously described.

Should a P-wave not be sensed before the timing out of the P-track interval (block 186), then an A-pulse is generated (block 188). The A-pulse is followed by an AV delay (block 190), which AV delay may have a slightly different value than the PV delay, as is known in the art. When the AV delay times out, a V-pulse is generated (block 194), followed by the PVARP (block 158, FIG. 13-1). The process then continues subsequent to the PVARP as described above (blocks 160, 162 et seq.).

If a P-wave is sensed during the timing out of the ALI (YES branch of block 174, FIG. 13-2), then a PV delay is started (block 196). Following the PV delay, two parallel paths begin. In a first path, the PV delay is monitored, and when it times out (block 198), a V-pulse to be generated (block 200). The first path then ends. In a Second path, the ALI is monitored (block 202), and when it times out, a phantom P-wave is assumed (block 204). A phantom P-wave is a signal that triggers various timed events within the pacemaker circuitry just as though an actual P-wave had been sensed, when in fact no P-wave was sensed. Following the phantom P-wave, a phantom PV delay begins (block 206). Following the PV phantom PV delay, a phantom V-pulse is assumed (block 210). A phantom V-pulse, like a phantom P-wave, is a signal that triggers various timed events within the pacemaker circuitry just as though an actual V-pulse had been generated and delivered to the heart when in fact no V-pulse is delivered to the heart. Following the phantom V-pulse, the PVARP begins (block 158), and the process continues as described above (blocks 160, 162 et seq.).

Figure 14:
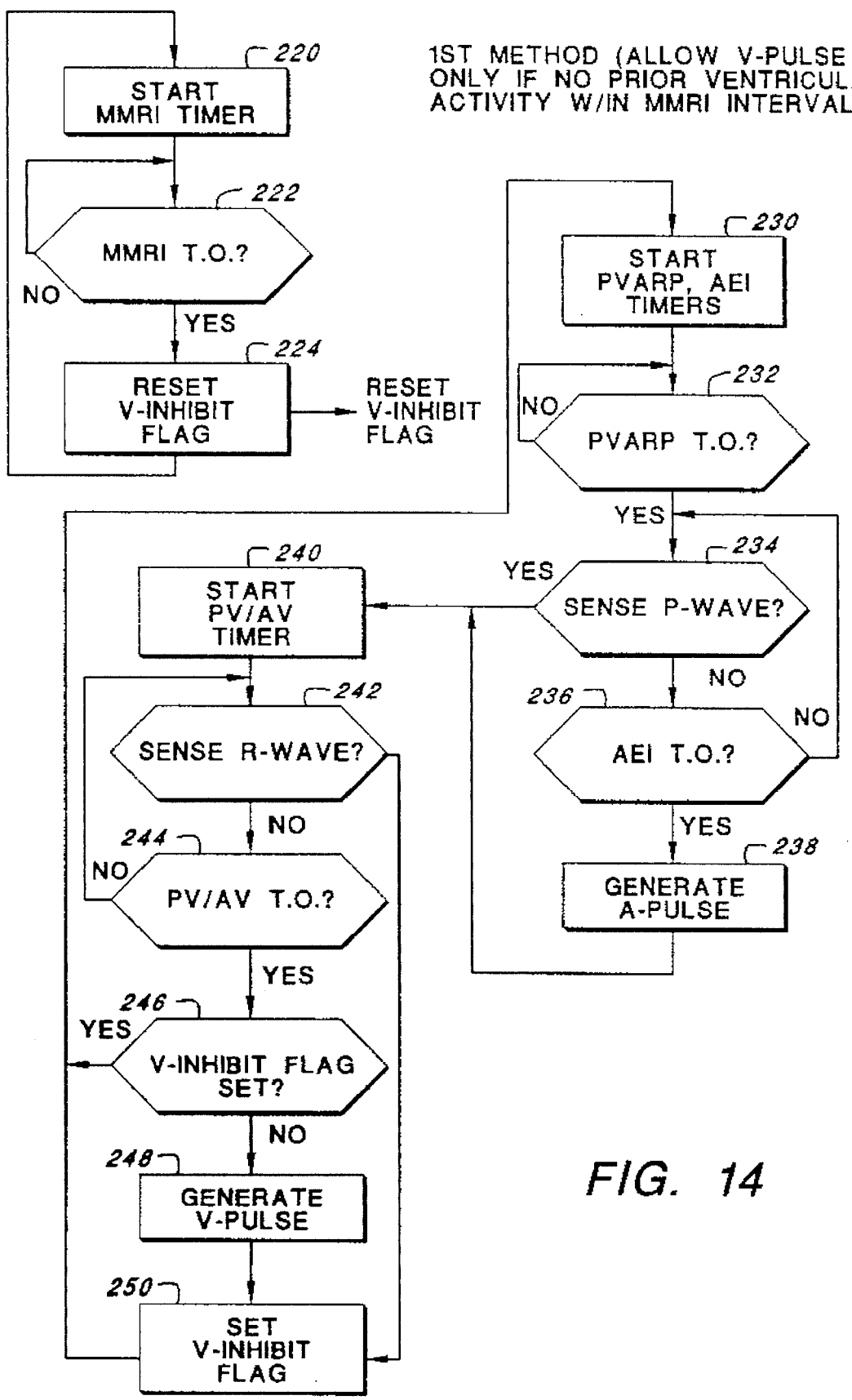
FIG. 14 shows a flowchart that illustrates the free-running MMRI approach of atrial lock interval pacing as shown in FIG. 11.

Next, turning to FIG. 14, a flowchart of the MMRI free-running technique corresponding to FIG. 11 (allowing only one V-pulse per MMRI) is shown. Two independent paths are shown. In a first path, shown on the upper left, an MMRI timer is started (block 220). When the MMRI timer times out (block 222), then a V-Inhibit Flag is reset (block 224). Then the process repeats. In a second path, shown generally on the right and below the first path, the conventional PVARP and Atrial Escape Interval (AEI) timers associated with a pacing cycle begin (block 230). When the PVARP times out (block 232), a determination is made as to whether a P-wave is sensed (block 234) before the AEI times out (blocks 234, 236). If no P-wave is sensed before the AEI times out, then an A-pulse is generated (block 238). If a P-wave is sensed, or after an A-pulse is generated, the PV/AV timer is started (block 240). A determination is then made as to whether an R-wave occurs before the timing out of the PV/AV timer (blocks 242, 244). If the PV/AV timer does time out without an R-wave having been sensed (block 244), and if the V-Inhibit flag is not set (NO branch of block 246), which means no V-pulse has yet been generated in the current MMRI, then a V-pulse is generated (block 248) and the V-Inhibit Flag is set (block 250). The current pacing cycle then ends, and the next pacing cycle begins (blocks 230, 232, et seq.).

Should the V-Inhibit flag be set (YES branch of block 246) when the PV/AV timer times out (block 244), that means a V-pulse has already been generated during the current MMRI. Hence, no V-pulse is generated, yet the next pacing cycle begins (blocks 230, 232, et seq.), and the process repeats.

Thus, using the method shown in FIG. 14, it is seen that at the conclusion of the MMRI, the V-inhibit flag is reset. At the generation of a V-pulse, the V-inhibit flag is set. Thus, the V-inhibit flag toggles between a set and reset state, and thereby limits the number of V-pulses that may occur during each MMRI to one.

Figure 15:
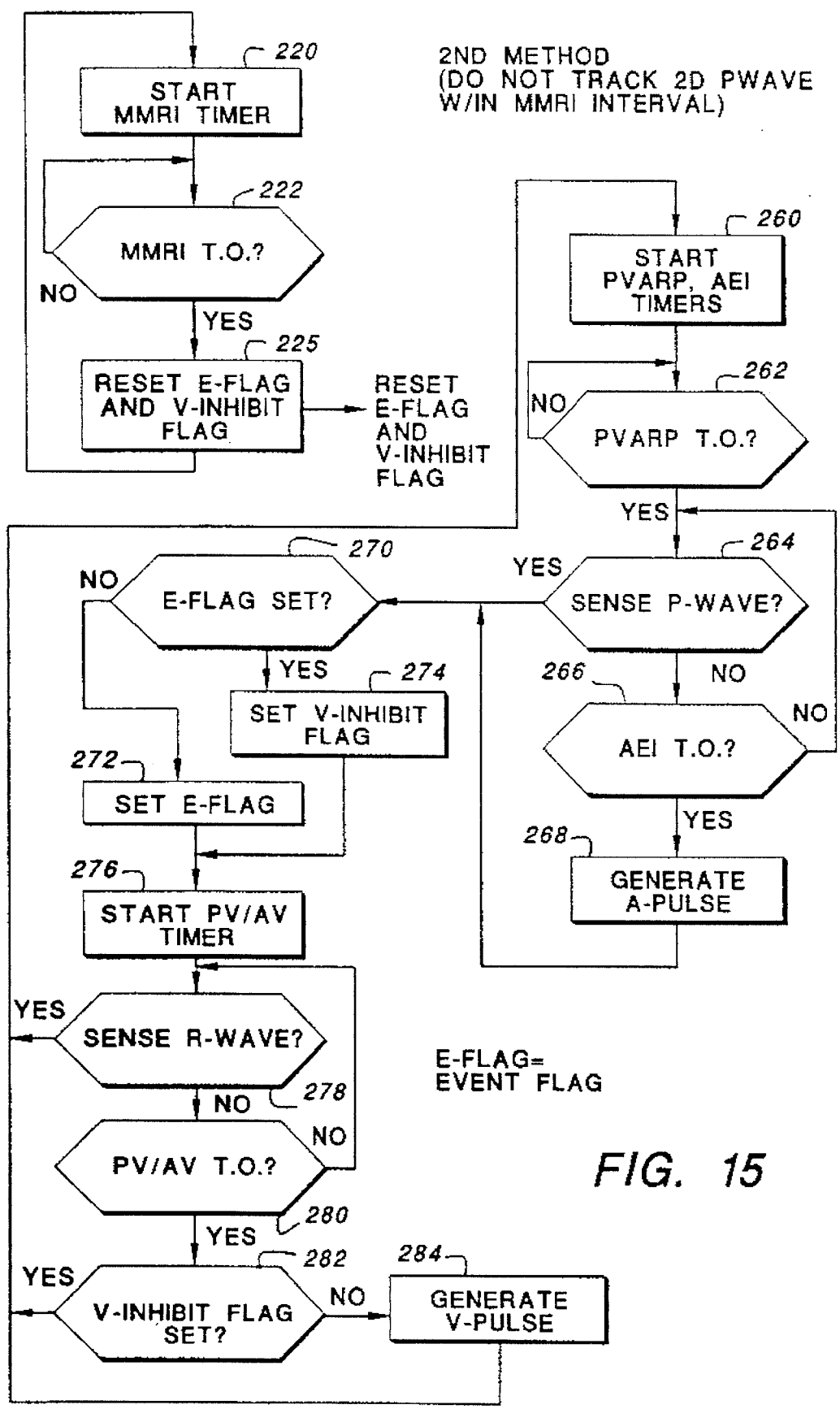
FIG. 15 similarly shows a flowchart that depicts the free-running MMRI approach of atrial lock interval pacing as shown in FIG. 12.

Referring next to FIG. 15, a flowchart of the MMRI free-running technique corresponding to FIG. 12 (tracking only one P-wave per MMRI) is shown. As with FIG. 14, two independent paths are shown. In a first path, shown on the upper left, an MMRI timer is started (block 220). When the MMRI timer times out (block 222), then an E-Flag (Event Flag) and V-Inhibit Flag are reset (block 225). Then the process repeats, with the E-Flag and V-Inhibit Flag being reset at the end of each MMRI. In a second path, shown generally on the right and below the first path, the conventional PVARP and Atrial Escape Interval (AEI) timers associated with a pacing cycle begin (block 260). When the PVARP times out (block 262), a determination is made as to whether a P-wave is sensed (block 264) before the AEI times out (blocks 264, 266). If no P-wave is sensed before the AEI times out, then an A-pulse is generated (block 268). If a P-wave is sensed, or after an A-pulse is generated, a determination is made as to whether the. E-Flag is set (block 270). If so (YES branch of block 270), a V-Inhibit Flag is set (block 274). If not (NO branch of block 270), the E-Flag is set (block 272), thereby indicating that an atrial event (P-wave or A-pulse) has occurred. The PV/AV timer is then started (block 276). A determination is then made as to whether an R-wave occurs before the timing out of the PV/AV timer (blocks 278, 280). If the PV/AV timer does time out without an R-wave having been sensed (block 280), and if the V-Inhibit flag is not set (NO branch of block 282), which means no atrial event has yet occurred in the current MMRI, then a V-pulse is generated (block 284). The current pacing cycle then ends, and the next pacing cycle begins (blocks 260, 262, et seq.). If the V-Inhibit flag is set (YES branch of block 282), then that means a second P-wave has already occurred in the current MMRI, so no V-pulse is generated (i.e., the second P-wave is not tracked), and the next pacing cycle beings (blocks 260, 262 et seq.).

In the manner described in FIG. 15, it is thus seen that only one P-wave is tracked during each MMRI. Such action limits the average ventricular rate to the MMR rate.

Turning next to FIGS. 16–19, some quantitative data evidencing operation of the present invention are presented. Such graphs thus provide a convenient graphical representation of the benefits that accrue from using the invention.

Figure 16:
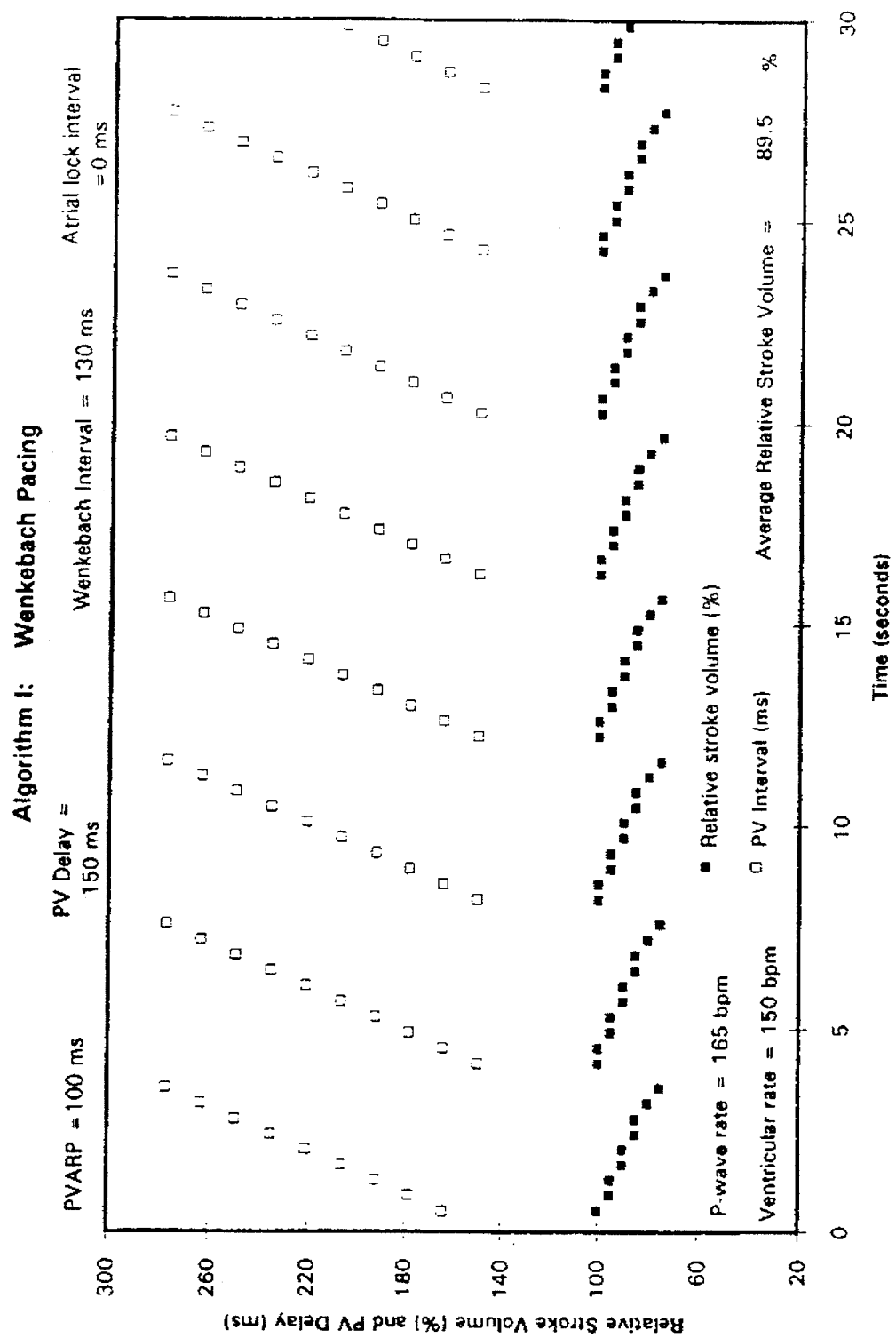
FIG. 16 is a graph illustrating relative stroke volume as a function of PV delay during Wenkebach Pacing (with ALI=0), and shows that (for the conditions shown) the average relative stroke volume is on the order of 90%.

In FIG. 16, a graph is presented that illustrates relative stroke volume as a function of PV delay during Wenkebach Pacing (i.e., with the ALI set equal to zero). In other words, the data presented in FIG. 16 illustrates the performance achieved without the invention (because atrial lock interval is blocked by making the ALI=0). In FIG. 16, the WI is set to 130 ms, PVARP is set to 100 ms, and the PV delay is set to 150 ms. As the data shows, under such conditions, and with the P-rate at 165 bpm, the ventricular rate averaged 150 bpm. The Stroke volume is dependent upon the PV interval as presented, e.g., by Haskell et al., "Optimum AV Interval in Dual-chamber Pacemakers," PACE, Vol. 9, pp. 670–675 (1986). As the PV delay becomes less optimal, the stroke volume decreases. The mean stroke volume obtained was 89.5% of the maximum stroke volume obtainable.

Figure 17:
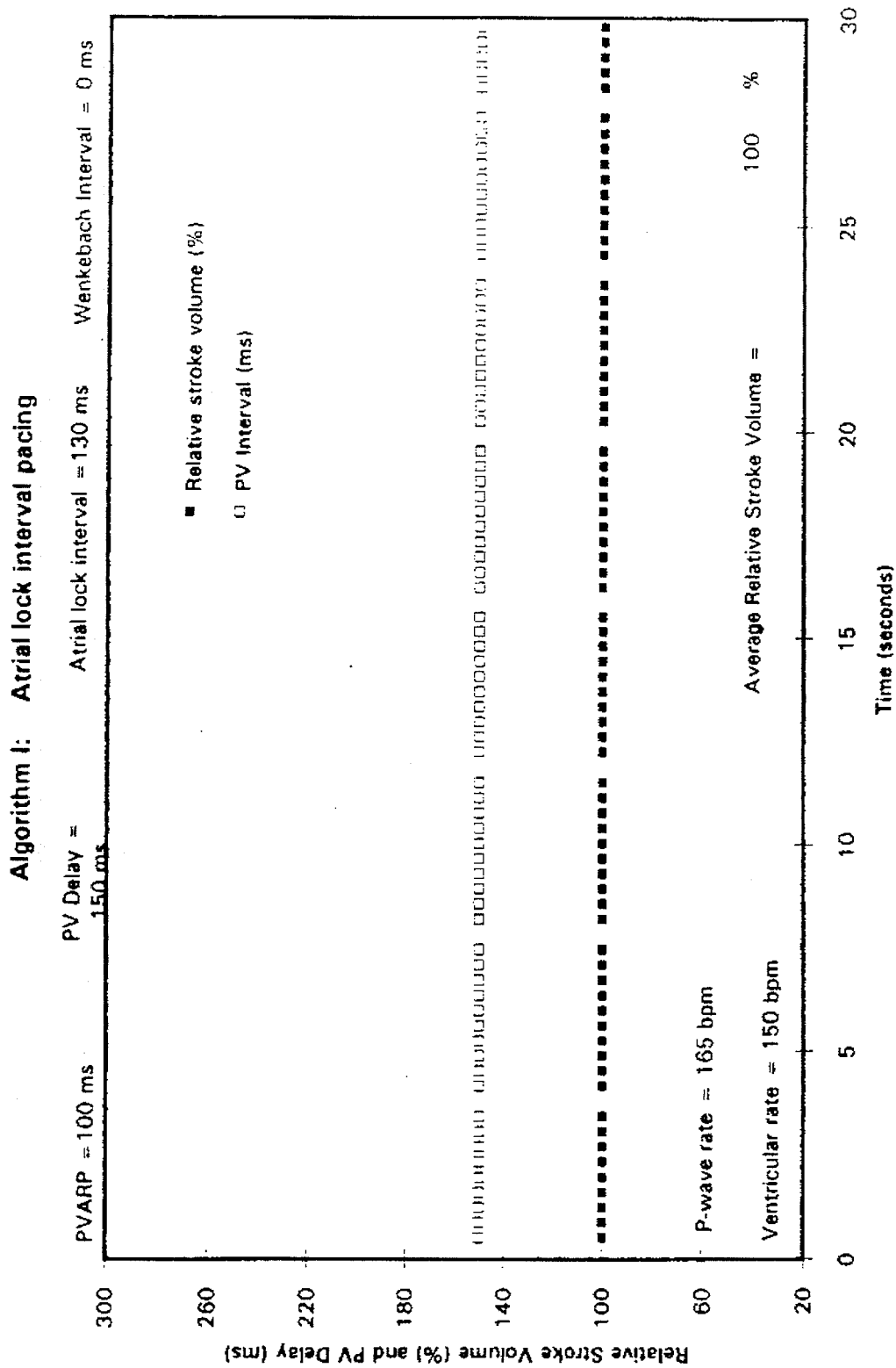
FIG. 17 is a graph illustrating relative stroke volume for a PV delay of 150 msec and an atrial lock interval of 130 msec (with the Wenkebach interval=0), and shows that (for the conditions shown) the average relative stroke volume approaches 100%.

Turning next to FIG. 17, a graph is presented that illustrates relative stroke volume as a function of PV delay during atrial lock interval pacing. For the data shown in FIG. 17, the Wenkebach phenomena was avoided by setting the WI to zero. The ALI was set to 130 ms. PVARP, PV delay, average ventricular rate and atrial rates and stroke volume dependence of PV interval were the same as in FIG. 16. As seen in FIG. 17, with atrial lock interval pacing, the mean stroke volume approaches 100% of the maximum stroke volume obtainable.

Figure 18:
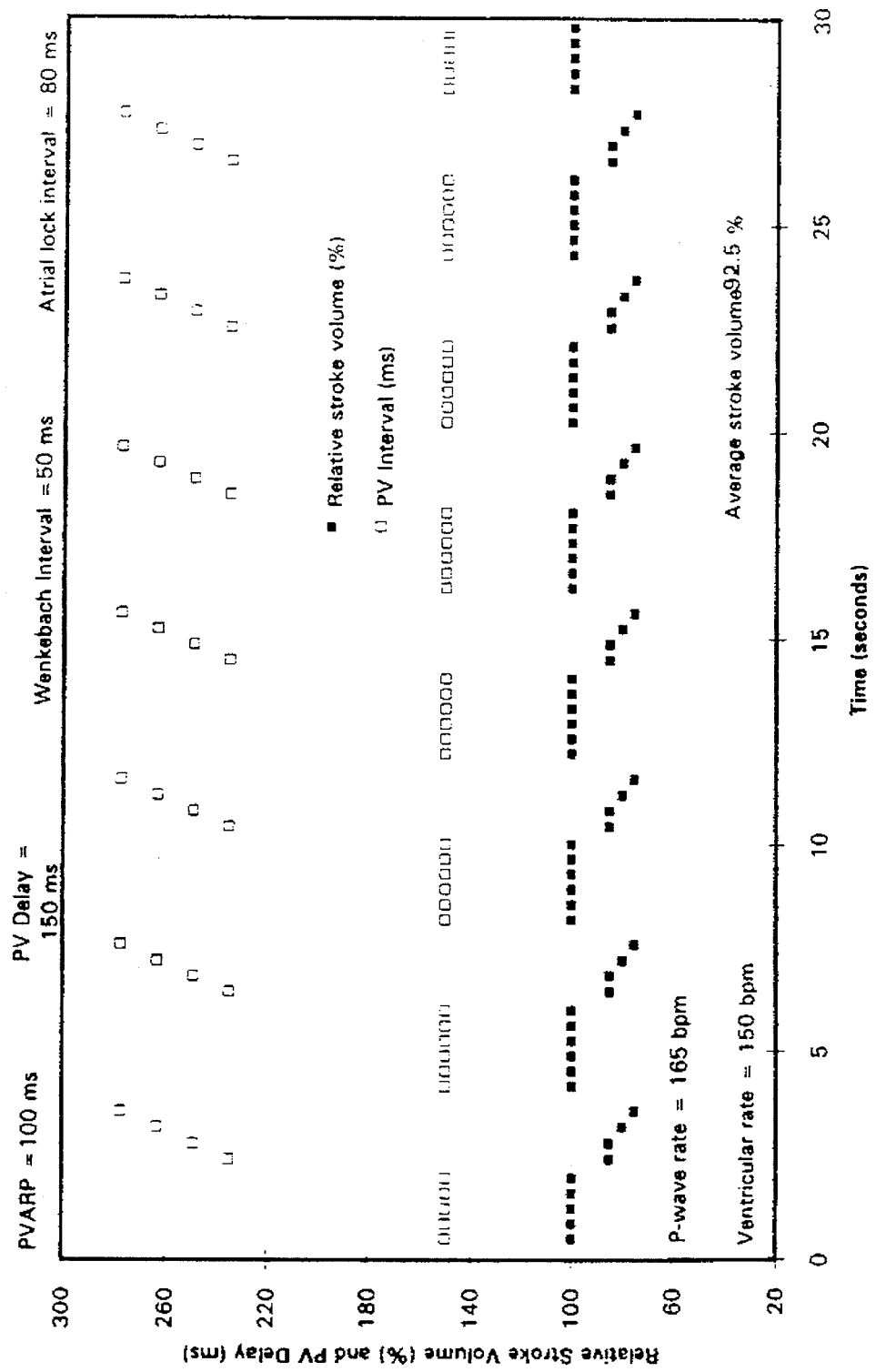
FIG. 18 is a graph illustrating atrial lock interval pacing in combination with Wenkebach pacing, and shows that (for the conditions shown) the average stroke volume is on the order of 92.5%.

In FIG. 18, a graph illustrating atrial lock interval pacing in combination with Wenkebach pacing is presented. WI was set to 50 ms, while ALI was set to 80 ms. PVARP, PV delay, average ventricular rate and atrial rates and stroke volume dependence of PV interval were the same as in FIG. 16. With this combination of Wenkebach and ALI pacing, the mean stroke volume approaches 92.5% of the maximum. This is a noticeable improvement over Wenkebach alone (FIG. 16), but not as good as ALI pacing alone (FIG. 17).

Figure 19:
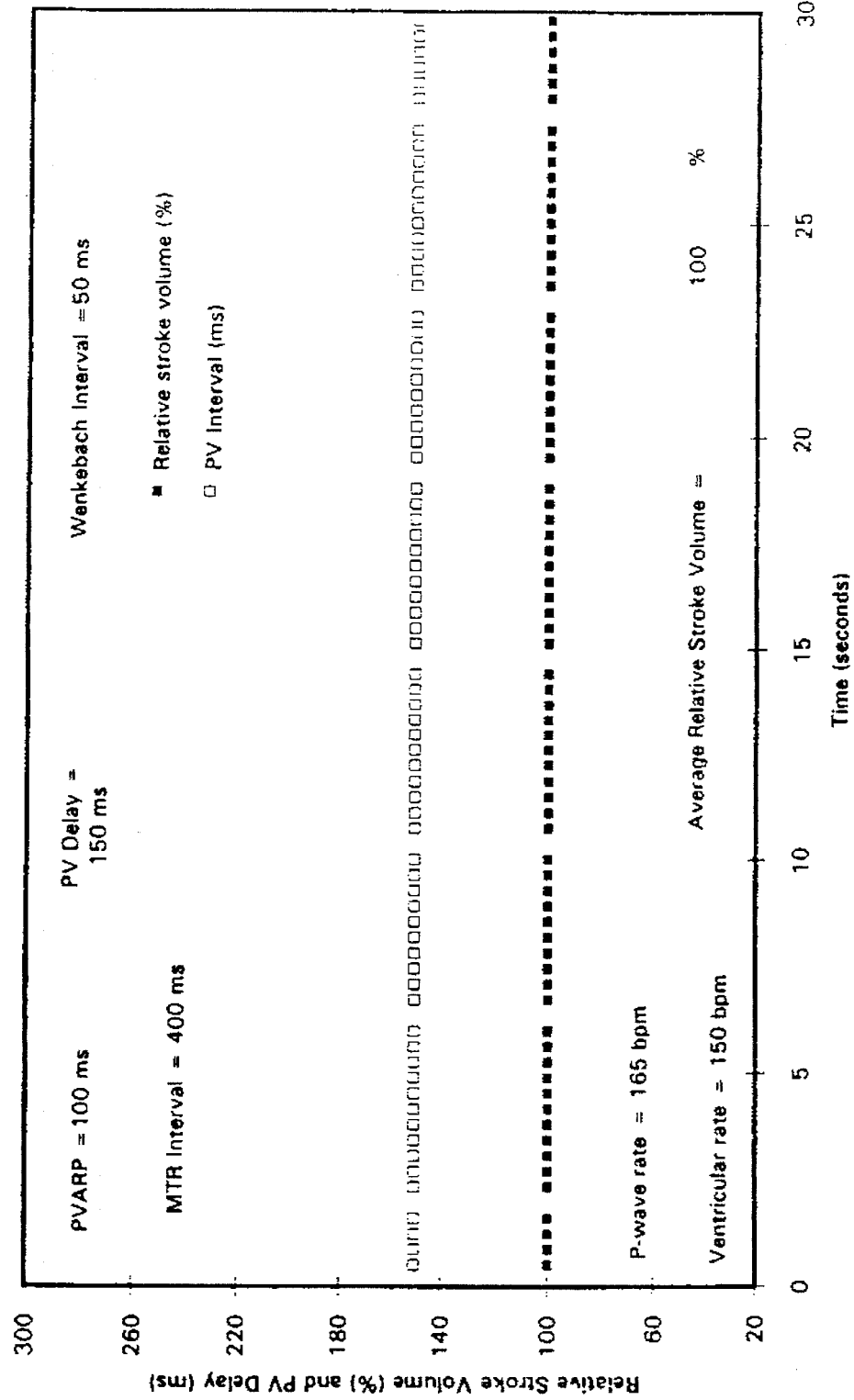
FIG. 19 graphically depicts atrial lock interval pacing in accordance with a free-running MMRI, and shows that (for the conditions shown) the average stroke volume is 100%.

FIG. 19 graphically depicts atrial lock interval pacing using a free-running MMRI that only allows one ventricular event in the MMRI, e.g., as described above in FIGS. 11 and 14. FIG. 19 shows that with MMRI set to 400 ms (Ventricular rate=150 bpm), and with the other conditions as shown (same as FIG. 16) the average stroke volume approaches 100%. Note that for the case shown in FIG. 19, there was no Wenkebach phenomena because the maximum atrial tracking rate is 1/(PVI+PVARP+WI)=200 bpm.

FIGS. 17–19 illustrate that although two quite different embodiments may be used to achieve the atrial lock interval pacing (or modified P-wave tracking at upper rates) in accordance with the present invention—the ALI approach of FIGS. 9-1 through 9-3, or equivalents thereof, or the free-running MMRI approach of FIGS. 11–12—very similar results are achieved. That is, A-V synchrony is maintained for longer periods of time at upper rates, resulting in improved stroke volume.

As has thus been described, it is seen that the present invention improves the upper rate performance of a pacemaker by synchronizing the atrial sensed events to the ventricular paced events for a higher percentage of the time when operating at the upper rates.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of operating a dual-chamber pacemaker in a P-tracking mode that maintains synchrony between atrial and ventricular events for a higher percentage of the time when operating at upper rate limits, the pacemaker including means for sensing P-waves and R-waves, and means for generating V-pulses, the method comprising:

tracking P-waves by generating a V-pulse one PV delay after sensing a P-wave, unless an R-wave is sensed prior to the end of the PV delay, in which case no V-pulse is generated, up to a first maximal tracking rate, whereby an instantaneous ventricular rate is limited by the first maximal tracking rate; and limiting a maximal mean ventricular rate to a second maximal tracking rate, said second maximal tracking rate being less than the first maximal tracking rate.

2. The method of claim 1, wherein the step of limiting the maximal mean ventricular rate to the second maximal tracking rate comprises:

setting a pacing interval for the pacemaker that is the sum of a PV delay, a post ventricular refractory period (PVARP), a Wenkebach interval (WI), an atrial lock interval (ALI) and a P-track interval; where the PV delay, PVARP, WI, ALI and P-track intervals are each set to a fixed value for any given cardiac cycle, but where the PV delay may be terminated early by sensing an R-wave prior to its termination, and where the P-track interval may also be terminated early by sensing a P-wave prior to its termination;

starting a pacing interval upon sensing a P-wave by beginning the PV delay;

starting the PVARP at the end of the PV delay;

starting the WI at the end of the PVARP;

starting the ALI at the end of the WI;

sensing whether a P-wave occurs during either the WI or ALI, and if so, tracking the sensed P-wave in a first delayed manner; and if a P-wave is not sensed during either the WI or ALI, then starting the P-track interval at the end of the ALI;

the first maximal tracking rate comprising 1/(PVD+PVARP+WI), and the second maximal tracking rate comprising 1/(PVD+PVARP+WI+ALI), where PVD is the PV delay.

3. The method of claim 2, wherein tracking the sensed P-wave in a first delayed manner comprises:

if a P-wave is sensed during the WI, starting a new pacing interval at the end of the ALI following the WI during which the P-wave was sensed; and if a P-wave is sensed during the ALI, immediately starting a second PV delay and generating a V-pulse at the conclusion of the second PV delay.

4. The method of claim 3 further including, if a P-wave is sensed during the ALI, and after immediately starting the second PV delay, continuing to time out the ALI during which the P-wave was sensed, and starting a new pacing interval at the end of the ALI, and inhibiting the generation of a V-pulse at the end of the PV delay of the new pacing interval.

5. The method of claim 2, further including setting the WI to be 0 ms, whereby the ALI is started at the end of the PVARP.

6. The method of claim 1, wherein the step of limiting the maximal mean ventricular rate to the second maximal tracking rate comprises:

setting a pacing interval for the pacemaker that is the sum of a PV delay, a post ventricular refractory period (PVARP), an atrial lock interval (ALI), a Wenkebach interval (WI), and a P-track interval; where the PV delay, PVARP, ALI, WI, and P-track intervals are each set to a fixed value for any given cardiac cycle, but where the PV delay may be terminated early by sensing an R-wave prior to its termination, and where the P-track interval may also be terminated early by sensing a P-wave prior to its termination;

starting a pacing interval upon sensing a P-wave by beginning the PV delay;

starting the PVARP at the end of the PV delay;

starting the ALI at the end of the PVARP;

starting the WI at the end of the ALI;

sensing whether a P-wave occurs during either the ALI or WI, and if so, tracking the sensed P-wave in a first delayed manner; and if a P-wave is not sensed during either the ALI or WI, then starting the P-track interval at the end of the WI;

the first maximal tracking rate comprising 1/(PVD+PVARP+ALI), and the second maximal tracking rate comprising 1/(PVD+PVARP+ALI+WI), where PVD is the PV delay.

7. The method of claim 6, wherein tracking the sensed P-wave in a first delayed manner comprises:

if a P-wave is sensed during the ALI, immediately starting an extended PV delay and generating a V-pulse at the conclusion of the extended PV delay; and if a P-wave is sensed during the WI, starting a new pacing interval at the end of the WI during which the P-wave was sensed.

8. The method of claim 7, wherein the step of starting an extended PV delay comprises starting a new PV delay having a value equal to the prior PV delay plus the WI.

9. The method of claim 7, further including, if a P-wave is sensed during the ALI, and after immediately starting the extended PV delay, continuing to time out the ALI during which the P-wave was sensed, starting a new pacing interval at the end of the ALI that begins with a second extended PV delay, and inhibiting the generation of a V-pulse at the end of the second extended PV delay of the new pacing interval.

10. The method of claim 1, further comprising defining the first maximal tracking rate and the second maximal tracking rate to be respective fixed rates.

11. The method of claim 1, further comprising allowing either the first maximal tracking rate or the second maximal tracking rate to be a pseudorandom rate.

12. A method of limiting the maximal mean ventricular rate of a pacemaker, the pacemaker including sensing means for sensing P-waves, pulse generation means for generating V-pulses, and timing means for defining timed intervals, the method comprising:

generating a recurring cycle of maximum mean rate intervals (MMRI) of x seconds each that runs independent of any sensed events;

tracking only a first sensed P-wave in each MMRI by: (i) starting a PV delay upon the sensing of the first sensed P-wave in the MMRI, and (ii) generating a V-pulse at the conclusion of the PV interval; and not tracking any subsequent sensed atrial events that occur during the MMRI.

13. A method of limiting the maximal mean ventricular rate of a pacemaker, the pacemaker including sensing means for sensing P-waves and R-waves; pulse generation means for generating V-pulses; and timing means for defining timed intervals; and wherein an R-wave or a V-pulse comprises a ventricular event; the method comprising:

generating a recurring cycle of maximum mean rate intervals (MMRI) of x seconds each that runs independent of any sensed events; and allowing only one ventricular event in each MMRI.

14. A method of operating a dual-chamber pacemaker in a P-tracking mode at upper rate limits, the pacemaker including means for sensing P-waves and R-waves, and means for generating V-pulses, the method comprising:

tracking P-waves by generating a V-pulse one PV delay after sensing a P-wave up to a first upper rate limit, whereby an instantaneous ventricular rate is limited by the first upper rate limit; and limiting a maximal mean ventricular rate to a second upper rate limit that is less than the first upper rate limit, while allowing an instantaneous ventricular rate to exceed the second upper rate limit and approach the first upper rate limit.

15. The method, as set forth in claim 14, wherein the step of limiting the maximal mean ventricular rate to the second upper rate limit comprises:

setting a pacing interval for the pacemaker that is the sum of a PV delay, a post ventricular refractory period (PVARP), an atrial lock interval (ALI), a Wenkebach interval (WI), and a P-track interval; where the PV delay, PVARP, ALI, WI and P-track intervals are each set to a fixed value for any given cardiac cycle, and where the P-track interval may be terminated early by sensing a P-wave or R-wave prior to its termination;

starting a pacing interval upon sensing a P-wave by beginning the PV delay;

starting the PVARP at the end of the PV delay;

starting the ALI and WI intervals in a prescribed ALI/WI sequence at the end of the PVARP;

sensing whether a P-wave occurs during the ALI/WI sequence, and if so, tracking such P-wave in a delayed manner, and if not so, then starting the P-track interval at the end of the ALI/WI sequence;

the first upper rate limit being defined by 1/(PVD+ PVARP), and the second upper rate limit being defined by 1/(PVD+PVARP+ALI), where PVD is the PV delay.

16. The method, as set forth in claim 15, wherein starting the ALI and WI intervals in a prescribed sequence comprises starting the ALI at the end of the PVARP and then starting the WI at the end of the ALI.

17. The method, as set forth in claim 15, wherein starting the ALI and WI intervals in a prescribed sequence comprises starting the WI at the end of the PVARP and then starting the ALI at the end of the WI.

18. The method, as set forth in claim 14, wherein the step of limiting the maximal mean ventricular rate to the second upper rate limit comprises:

generating a free-running sequence of a recurring maximum mean rate interval (MMRI), each MMRI of the free-running sequence having a duration of T seconds, the MMRI sequence running asynchronously relative to any sensed P-waves, R-waves, or generated V-pulses;

tracking only a first sensed P-wave in each MMRI and not tracking any subsequent sensed P-waves that occur during the MMRI.

19. The method, as set forth in claim 18, further including setting T to be equal to 300 to 600 milliseconds.

20. The method, as set forth in claim 14, wherein the step of limiting the maximal mean ventricular rate to the second upper rate limit comprises:

generating a free-running sequence of a recurring maximum mean rate interval (MMRI), each MMRI of the free-running sequence having a duration of T seconds, the MMRI sequence running asynchronously relative to any sensed P-waves, R-waves or generated V-pulses; and allowing only one ventricular event in each MMRI, where a ventricular event comprises either an R-wave or a V-pulse.

21. The method, as set forth in claim 20, further including setting T to be equal to 300 to 600 ms.

22. In a dual-chamber pacemaker, a system for increasing stroke volume at upper pacemaker rates, the pacemaker including means for sensing P-waves and R-waves, and means for generating V-pulses, the system comprising:

P-wave tracking means for providing a ventricular rate that tracks sensed P-waves;

upper rate limiting means for limiting the P-wave tracking means so that P-waves are instantaneously tracked up to a maximal tracking rate, thereby providing an instantaneous ventricular rate that tracks the sensed P-waves up to the maximal tracking rate; and average-rate limiting means for limiting an average ventricular rate to a value that is less than the maximal tracking rate.

23. The system of claim 22, wherein the upper rate limiting means comprises timing means for defining a pacing interval for the pacemaker that is the sum of a PV interval (PVI), a post ventricular refractory period (PVARP), an atrial lock interval (ALI) and a P-track interval; and where the timing means sets the PV delay, PVARP, ALI and P-track interval to a specified value for any given cardiac cycle, but where at least the P-track interval may vary in value from cardiac cycle to cardiac cycle; and wherein the P-wave tracking means includes blocking means for blocking any P-wave that occurs during the PV delay or PVARP, and V-pulse response means for generating a V-pulse one PV delay after a P-wave that occurs during the ALI or P-track interval; and further wherein the means for limiting the average ventricular rate comprises means for generating a second PV interval at the conclusion of any ALI during which a P-wave occurs without generating a V-pulse at the conclusion thereof, and generating a second PVARP following the second PV delay, which second PV interval and second PVARP begin a next pacing interval;

whereby P-waves may be instantaneously tracked up to a maximal tracking rate that comprises 1/(PVI+ PVARP), yet the average ventricular rate is limited to a value that approaches 1/(PVI+PVARP+ALI).

24. The system of claim 23, wherein the timing means comprises means for defining the pacing interval to be the sum of the PVI, PVARP, ALI, P-track interval and a Wenkebach interval (WI), and wherein the P-wave tracking means further includes means for tracking a P-wave that occurs during the WI on a delayed basis.

25. The system of claim 24, wherein the timing means includes means for inserting the WI into the pacing interval so that it follows the ALI.

26. The system of claim 24, wherein the timing means includes means for inserting the WI into the pacing interval so that it follows the PVARP, with the ALI following the WI.

27. The system of claim 22, wherein the average rate limiting means comprises:

timing means for defining a maximum mean rate interval (MMRI);

free-running means for repeating the MMRI over and over without synchronization to any other events; and means for preventing more than one V-pulse from being generated during each MMRI;

whereby the average ventricular rate is limited to a value that is equal to 1/MMRI.

28. The system of claim 22, wherein the average rate limiting means comprises:

timing means for defining a maximum mean rate interval (MMRI);

free-running means for repeating the MMRI over and over without synchronization to any other events; and means for tracking one and only one P-wave during each MMRI;

whereby the average ventricular rate, which is set by the rate of the tracked P-waves, is limited to a value that is equal to 1/MMRI.

29. A dual-chamber implantable pacemaker operable in a P-tracking mode, the pacemaker including means for sensing P-waves, and means for generating V-pulses, comprising:

P-wave tracking means for providing a ventricular rate that tracks sensed P-waves;

upper rate limiting means for limiting the P-wave tracking means so that P-waves are tracked only up to a maximal tracking rate; and means for limiting a maximal mean ventricular rate to a value that is less than the maximal tracking rate.

30. A method of maintaining synchrony between atrial events and ventricular stimulation in an implantable pacemaker, the pacemaker having means for sensing atrial events, and means for generating a ventricular stimulation pulse (V-pulse), comprising:

(a) generating a recurring cycle of tracking periods of T seconds each that runs independent of any sensed events;

(b) tracking only a first sensed atrial event in each tracking period by: (i) starting a PV interval upon the sensing of the first sensed atrial event in the tracking period, and (ii) generating a V-pulse at the conclusion of the PV interval; and (c) not tracking any subsequent sensed atrial events that occur during a tracking period wherein a first sensed atrial event has already been tracked;

whereby the average rate of generating V-pulses in synchrony with sensed atrial events is 1/T pulses per second.

31. The method of claim 30, wherein T comprises a period of time ranging from 300 to 600 milliseconds.

32. The method of claim 30, wherein the pacemaker includes means for determining a pacing interval, and further including using the method set forth in claim 30 only when the pacing interval is less than a programmable threshold of y seconds, where the programmable threshold of y seconds is selected to define an upper rate limit above which the method is used, and below which the method is not used.

33. A method of maintaining synchrony between atrial events and ventricular stimulation in a dual-chamber implantable pacemaker, the pacemaker having means for sensing atrial events and ventricular events, and means for generating a ventricular stimulation pulse (V-pulse), said method comprising:

(a) generating a recurring cycle of tracking periods of T seconds each that runs independent of any sensed events;

(b) tracking a sensed atrial event in each tracking period by:

(i) starting a PV interval upon the sensing of the sensed atrial event in the tracking period, (ii) generating a V-pulse at the conclusion of the PV interval when ventricular activity has not already occurred during the tracking period, and (iii) inhibiting the generation of a V-pulse at the conclusion of the PV interval when ventricular activity has already occurred during the tracking period;

whereby the average rate of generating V-pulses in synchrony with sensed atrial events is 1/T pulses per second.

34. The method of claim 33, wherein T comprises a period of time ranging from 300 to 600 msec.

35. A method of operating an implantable pacemaker to synchronize atrial depolarization with a paced ventricular depolarization, said pacemaker including means for sensing atrial and ventricular depolarizations, and means for generating a ventricular stimulation pulse (V-pulse) at a set time following the atrial depolarization, the V-pulse being adapted to force a ventricular depolarization, the method comprising the steps of:

(a) defining a maximum mean rate interval (MMRI) that sets the fastest average rate at which the pacemaker is to pace a patient's heart;

(b) starting a recurring cycle of MMRI intervals by starting a first MMRI interval at any time, starting a second MMRI interval at the conclusion of the first MMRI interval, starting a third MMRI interval at the conclusion of the second MMRI interval, and so on, with an (n+1)th MMRI interval being started at the conclusion of an nth MMRI interval, where n is an integer, with the cycle of MMRI intervals thus established running independent of other timed or sensed events within the pacemaker; and (c) generating a V-pulse at the set time following the atrial depolarization no more than once during each MMRI interval.

36. The method of claim 35, wherein the step of generating the V-pulse no more than once during each MMRI comprises:

(1) monitoring the number of atrial depolarizations that occur during each MMRI, (2) starting a PV interval upon the occurrence of the first atrial depolarization of each MMRI, but not starting the PV interval upon the occurrence of any subsequent atrial depolarization within such MMRI, and (3) generating the V-pulse at the conclusion of the PV interval.

37. The method of claim 35, wherein the step of generating the V-pulse no more than once during each MMRI comprises:

(1) monitoring each MMRI for the occurrence of a ventricular depolarization, and (2) inhibiting the generation of any V-pulse that would cause a second ventricular depolarization to occur within an MMRI during which a prior V-pulse was generated.

38. The method of claim 37, wherein the MMRI has a value of between 300 and 600 milliseconds.

39. A dual-chamber implantable pacemaker comprising:

sensing means for sensing an atrial depolarization (P-wave) and a ventricular depolarization (R-wave) within a patient's cardiac cycle;

pulse generating means for generating a ventricular stimulation pulse (V-pulse);

control means for controlling the sensing means and pulse generating means so as to maximize the number of cardiac cycles during which the generation of a V-pulse is synchronized with atrial activity, said control means including:

means for generating a PV interval that defines the time between a sensed P-wave and a V-pulse, means for inhibiting the generating of a V-pulse at the conclusion of the PV interval in the event an R-wave is sensed before the timing out of the PV interval, means for generating a cycle of maximum mean rate intervals (MMRI's) that runs asynchronously relative to the sensing means and pulse generating means, with a new MMRI commencing at the conclusion of a prior MMRI, and means for preventing the generation of a V-pulse within a given MMRI of the cycle of MMRI's if either an R-wave or V-pulse has already occurred within the given MMRI, whereby at most only one ventricular depolarization is caused by said pacemaker during each MMRI.

40. The dual-chamber implantable pacemaker, as set forth in claim 39, wherein the means for preventing the generation of a V-pulse within a given MMRI comprises means for starting a PV interval following only a first P-wave of a given MMRI, and not starting the PV interval following a subsequent P-wave of the given MMRI, whereby the subsequent P-wave of the given MMRI is ignored and does not result in the generation of a V-pulse.

41. The dual-chamber implantable pacemaker, as set forth in claim 39, wherein the means for preventing the generation of a V-pulse within a given MMRI comprises means for counting the number of ventricular depolarizations that occur within a given MMRI, and means for inhibiting the generation of any V-pulse which would result in the generation of a second V-pulse within the given MMRI.

42. The dual-chamber implantable pacemaker, as set forth in claim 39, wherein said MMRI comprises a programmable interval that is set to a value of between 300 to 600 milliseconds.

43. The dual-chamber implantable pacemaker, as set forth in claim 39, wherein the pacemaker further includes means for sensing a physiological parameter, and wherein said MMRI comprises a variable interval that varies between 300 to 600 milliseconds as a function of the physiological parameter.

44. The dual-chamber implantable pacemaker, as set forth in claim 39, wherein said control means further includes:

means for determining an atrial rate, the atrial rate being determined as a function of the average time interval between atrial depolarizations, means for adjusting the PV interval as a function of the atrial rate, with PV interval being made shorter as the atrial rate increases.

45. A dual-chamber pacemaker for stimulating the heart of a patient, said pacemaker comprising:

an atrial channel that includes means for sensing P-waves;

a ventricular channel that includes means for sensing R-waves and means for generating and delivering ventricular stimulation pulses (V-pulses);

control means for controlling the atrial channel and the ventricular channel to operate in a dual-chamber mode of operation, said control means comprising:

timing means for defining a pacing cycle made up of a plurality of timed periods, said timed periods including a post ventricular atrial refractory period (PVARP) that begins with a ventricular event, said ventricular event comprising either a sensed R-wave or a generated V-pulse, and upper rate limiting means for limiting the maximum mean rate of the pacing cycle, the maximum rate being defined by a maximum mean rate interval (MTR), said upper rate limiting means comprising:

means for generating a continuous MMRI sequence with one MMRI beginning immediately after the conclusion of a preceding MMRI, said MMRI sequence being asynchronous relative to said timing means, and means for limiting the number of V-pulses that may occur during each MMRI of the sequence to no more than one, whereby V-pulses may not be generated by the ventricular channel at a rate that is, on average, any faster than the maximum rate defined by the MMRI.

* * * * *